(12) United States Patent
Zalzman et al.

(10) Patent No.: US 11,957,718 B2
(45) Date of Patent: Apr. 16, 2024

(54) METHODS FOR GENERATING MULTIPOTENT STEM CELLS FROM TONSILLAR BIOPSIES

(71) Applicant: University of Maryland, Baltimore, Baltimore, MD (US)

(72) Inventors: Michal Zalzman, Baltimore, MD (US); Rodney Taylor, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 826 days.

(21) Appl. No.: 16/472,477

(22) PCT Filed: Dec. 22, 2017

(86) PCT No.: PCT/US2017/068094
§ 371 (c)(1),
(2) Date: Jun. 21, 2019

(87) PCT Pub. No.: WO2018/119349
PCT Pub. Date: Jun. 28, 2018

(65) Prior Publication Data
US 2021/0128628 A1 May 6, 2021

Related U.S. Application Data

(60) Provisional application No. 62/438,107, filed on Dec. 22, 2016.

(51) Int. Cl.
| | |
|---|---|
| *C12N 5/077* | (2010.01) |
| *A61K 35/28* | (2015.01) |
| *A61K 35/32* | (2015.01) |
| *A61K 35/34* | (2015.01) |
| *A61L 27/38* | (2006.01) |
| *C12N 5/0775* | (2010.01) |
| *C12N 9/52* | (2006.01) |
| *C12N 9/54* | (2006.01) |

(52) U.S. Cl.
CPC .............. *A61K 35/28* (2013.01); *A61K 35/32* (2013.01); *A61K 35/34* (2013.01); *A61L 27/3834* (2013.01); *A61L 27/3895* (2013.01); *C12N 5/0653* (2013.01); *C12N 5/0654* (2013.01); *C12N 5/0655* (2013.01); *C12N 5/0668* (2013.01); *C12N 9/52* (2013.01); *C12N 9/54* (2013.01); *C12N 2506/1392* (2013.01)

(58) Field of Classification Search
None
See application file for complete search history.

(56) References Cited

U.S. PATENT DOCUMENTS 8,883,499 B2 * 11/2014 Hedrick ................. C12M 47/04
606/1
2008/0095748 A1 4/2008 Kharazi 2012/0034611 A1 2/2012 Nagasawa
2015/0037289 A1 2/2015 Khan
2015/0267167 A1 9/2015 Furcht

FOREIGN PATENT DOCUMENTS

CN 105247052 1/2016

OTHER PUBLICATIONS

Janjanin et al, Arthritis Research & Therapy, 2008, 10:R83 (Year: 2008).*
Baksh et al., "Comparison of Proliferative and Multilineage Differentiation Potential of Human Mesenchymal Stem Cells Derived from Umbilical Cord and Bone Marrow", Stem Cells, vol. 25 (Mar. 1, 2007), pp. 1384-1392.
Bell et al., "Pericytes Control Key Neurovascular Functions and Neuronal Phenotype in the Adult Brain and during Brain Aging", Neuron, vol. 68, No. 3 (Nov. 4, 2010), pp. 409-427.
Buckner et al., "Marrow Harvesting From Normal Donors", Blood, vol. 64, No. 3 (Sep. 1984), pp. 630-634.
Cho et al., "Tonsil-derived mesenchymal progenitor cells acquire a follicular dendritic cell phenotype under cytokine stimulation", Cytokine, vol. 59, No. 2 (May 10, 2012), pp. 211-214.
Choi et al., "Effects of Donor Age, Long-Term Passage Culture, and Cryopreservation on Tonsil-Derived Mesenchymal Stem Cells", Cell Physiology and Biochemistry, vol. 36, No. 1 (Apr. 27, 2015), pp. 85-99.
Crisan et al., A perivascular origin for mesenchymal stem cells in multiple human organs, Cell Stem Cell, vol. 3, No. 3 (Sep. 11, 2008), pp. 301-313.
De Bari et al., "A Biomarker-Based Mathematical Model to Predict Bone-Forming Potency of Human Synovial and Periosteal Mesenchymal Stem Cells", Arthritis & Rheumatism, vol. 58, No. 1 (Jan. 2008), pp. 240-250.
De Coppi et al., "Isolation of amniotic stem cell lines with potential for therapy", Nature Biotechnology, vol. 25, No. 1 (Jan. 7, 2007), pp. 100-106.
Ding et al., "Mesenchymal Stem Cells", Cell Transplantation, vol. 20 (Feb. 1, 2011), pp. 5-14.
Dominici et al., "Minimal criteria for defining multipotent mesenchymal stromal cells. The International Society for Cellular Therapy position statement", Cytotherapy, vol. 8, No. 4 (2006), pp. 315-317.
Francis et al., "Isolating adipose-derived mesenchymal stem cells from lipoaspirate blood and saline fraction", Organogenesis, vol. 6, No. 1 (Jan. 2010), pp. 11-14.
Friedenstein et al., "The Development of Fibroblast Colonies in Monolayer Cultures of Guinea-Pig Bone Marrow and Spleen Cells", Cell Proliferation, vol. 3, No. 4 (Jan. 20, 1970), pp. 393-403.
Fukuchi et al., "Human Placenta-Derived Cells Have Mesenchymal Stem/Progenitor Cell Potential", Stem Cells, vol. 22, No. 5 (Sep. 1, 2004), pp. 649-658.

(Continued)

*Primary Examiner* — Allison M Fox
(74) *Attorney, Agent, or Firm* — Riverside Law LLP

(57) ABSTRACT

The invention provides compositions comprising multipotent progenitor cells isolated from tonsillar tissue and differentiated cells derived therefrom and methods for using the cells for the treatment of diseases or disorders.

6 Claims, 5 Drawing Sheets
(4 of 5 Drawing Sheet(s) Filed in Color)
Specification includes a Sequence Listing.

(56) References Cited

OTHER PUBLICATIONS

Gargett et al., "Isolation and Culture of Epithelial Progenitors and Mesenchymal Stem Cells from Human Endometrium", Biology of Reproduction, vol. 80, No. 6 (Feb. 18, 2009), pp. 1136-1145.
Heidari et al., "Comparison of proliferative and multilineage differentiation potential of sheep mesenchymal stem cells derived from bone marrow, liver, and adipose tissue", Avicenna Journal of Medical Biotechnology, vol. 5, No. 2 (Apr. 2013), pp. 104-117.
Heino et al., "Differentiation of osteoblasts and osteocytes from mesenchymal stem cells", Current Stem Cell Research and Therapy, vol. 3, No. 2 (Jun. 2008), pp. 131-145.
Heo et al., "Comparison of molecular profiles of human mesenchymal stem cells derived from bone marrow, umbilical cord blood, placenta and adipose tissue", International Journal of Molecular Medicine, vol. 37, No. 1 (Nov. 19, 2015), pp. 115-125.
Jin et al., "Comparative analysis of human mesenchymal stem cells from bone marrow, adipose tissue, and umbilical cord blood as sources of cell therapy", International Journal of Molecular Sciences, vol. 14, No. 9 (Sep. 3, 2013), pp. 17986-18001.
Johnstone et al., "In vitro chondrogenesis of bone marrow-derived mesenchymal progenitor cells", Experimental Cell Research, vol. 238, No. 1 (Jan. 10, 1998)., pp. 265-272.
Kim et al., "Characterisation of insulin-producing cells differentiated from tonsil derived mesenchymal stem cells", Differentiation, vol. 90, No. 1-3 (Sep. 29, 2015), pp. 27-39.
Kim et al., "Clinical applications of mesenchymal stem cells", The Korean Journal of Internal Medicine, vol. 28, No. 4 (Jul. 1, 2013), pp. 387-402.
Le Blanc et al., "Immunobiology of human mesenchymal stem cells and future use in hematopoietic stem cell transplantation", Biology of Blood and Marrow Transplantation, vol. 11 (May 2005), pp. 321-334.
Lee et all., "Isolation and Localization of Mesenchymal Stem Cells in Human Palatine Tonsil by W5C5 (SUSD2)", Cellular Physiology and Biochemistry, vol. 38, No. 1 (Jan. 8, 2016), pp. 83-93.
Murphy et al., "Mesenchymal stem cells: environmentally responsive therapeutics for regenerative medicine", Experimental & Molecular Medicine, vol. 45 (Nov. 15, 2013), e54.
Murray et al., "Natural history of mesenchymal stem cells, from vessel walls to culture vessels", Cell Mol Life Sci, vol. 71 (Oct. 25, 2013), pp. 1353-1374.
Nishimori et al., "Health-related quality of life of unrelated bone marrow donors in Japan", Blood, vol. 99, No. 6 (Mar. 15, 2002), pp. 1995-2001.
Park et al., "Tonsil-derived Mesenchymal Stem Cells Ameliorate CCI4-induced Liver Fibrosis in Mice via Autophagy Activation", Nature Scientific Reports, vol. 5 (Feb. 27, 2015), Artical No. 8616.
Pittenger et al., "Multilineage Potential of Adult Human Mesenchymal Stem Cells", Science, vol. 284, No. 5411 (Apr. 2, 1999), pp. 143-147.
Ryu et al., "Tonsil-derived mesenchymal stromal cells:evaluation of biologic, immunologic and genetic factors for successful banking", Cytotherapy, vol. 14, No. 10—(Nov. 2012), pp. 1193-1202.
Sacchetti et al., "No Identical "Mesenchymal Stem Cells" at Different Times and Sites: Human Committed Progenitors of Distinct Origin and Differentiation Potential Are Incorporated as Adventitial Cells in Microvessels", Stem Cell Reports, vol. 6, No. 6 (Jun. 14, 2016), pp. 897-913.
Scanu et al.,Evaluation of the use of human Mesenchymal Stem Cells for acute toxicity tests , Toxicology in Vitro, vol. 25, No. 8 (Jul. 26, 2011), pp. 1989-1995.
Tan et al., "Comparison of potentials of stem cells isolated from tendon and bone marrow for musculoskeletal tissue engineering", Tissue Engineering Part A, vol. 18 (Apr. 2012), pp. 840-851.
Yoo et al., "The chondrogenic potential of human bone-marrow-derived mesenchymal progenitor cells", The Journal of Bone and Joint Surgery American, vol. 80, No. 12 (Dec. 1998), pp. 1745-1757.
Zuk et al., "Human Adipose Tissue Is a Source of Multipotent Stem Cells", Molecular Biology of the Cell, vol. 13, No. 12 (Dec. 2002), pp. 4279-4295.

\* cited by examiner

METHODS FOR GENERATING MULTIPOTENT STEM CELLS FROM TONSILLAR BIOPSIES

CROSS REFERENCE TO RELATED APPLICATIONS

This application is a U.S. national phase application filed under 35 U.S.C. § 371 claiming benefit to International Patent Application No. PCT/US17/68094, filed Dec. 22, 2017, which is entitled to priority under 35 U.S.C. § 119(e) to U.S. Provisional Application No. 62/438,107, filed Dec. 22, 2016, which is hereby incorporated by reference herein in its entirety.

BACKGROUND OF THE INVENTION

Multipotent progenitor cells (MPCs) can give rise to several types of specialized cells (Pittenger et al., (1999) Science, 284:143-147). These fibroblast-like cells were first identified and isolated from the bone marrow (BM) and spleen (Friedenstein et al., (1970) Cell Tissue Kinet, 3:393-403). Presently, many other tissues such as placenta, amniotic fluid, umbilical cord, adipose tissue, tonsils and endometrium have been identified as sources of MPCs (Baksh et al., (2007) Stem Cells, 25:1384-92; De Coppi et al., (2007) Nat Biotechnol, 25:100-106; Fukuchi et al., (2004) Stem Cells, 22:649-658; Gargett et al., (2009) Biology of Reproduction, 80:1136-1145; Lee et al., (2016) Cell Physiol Biochem, 38:83-93; Park et al., (2015) Sci Rep, 5:8616; Ryu et al., (2012) Cytotherapy, 14:1193-1202; Zuk et al., (2002) Molecular Biology of the Cell, 13:4279-4295). Nevertheless, the phenotype and differentiation potency of MPCs vary with respect to the tissue source from which they are isolated and the harvesting procedure (Heidari et al., (2013) Avicenna J Med Biotechnol, 5:104-117; Heo et al., (2016) Int J Mol Med, 37:115-125; Tan et al., (2012) Tissue Eng Part A, 18:840-851). MPCs possess the potential to differentiate into multiple cell types including adipocytes (fat), chondrocytes (cartilage), and osteoblasts (bone) (Heino and Hentunen. (2008) Curr Stem Cell Res Ther, 3:131-145). Characterization of MPCs includes adherence to standard tissue culture plastic, expression of various surface antigens, and in vitro differentiation potential (Dominici et al., (2006) Cytotherapy, 8:315-317). Like other types of adult stem cells, MPCs remain quiescent (non-dividing) for long periods. When activated, MPCs divide and differentiate to replace injured cells and secrete factors to prevent inflammation and promote tissue repair (Murphy et al., (2013). Exp Mol Med, 45:e54).

Cellular therapies hold a great potential for the cure of a wide range of diseases and provide enhanced treatment modalities including immunomodulatory therapies, tissue regeneration and cancer therapies. Using MPCs is an attractive approach for cell therapy as it avoids the ethical and practical issues of embryonic and fetal-derived stem cells (Ding et al., (2011) Cell Transplant, 20:5-14). Importantly, MPCs migrate into sites of tissue injury and have strong immunosuppressive properties that can be exploited for successful autologous and for allogenic transplantation without the need of complex and harmful anti-rejection medication protocols (Murphy et al., (2013) Exp Mol Med, 45:e54; Le Blanc and Ringden, (2005) Biol Blood Marrow Transplant, 11:321-34). Currently, many clinical trials are testing MPCs obtained from different tissue sources for the treatment of numerous conditions such as autoimmunity, heart disease, bone and cartilage disease, cancer, neuropathologies and gastrointestinal diseases (Kim and Cho, (2013) Korean J Intern Med, 28:387-402). Human MPCs are also equally used in drug discovery applications as replacements for primary cells and animal models for initial toxicity and screening of new compounds (Scanu et al., (2011), Toxicology in Vitro, 25:1989-1995).

MPCs reside on blood vessels (Crisan et al., (2008) Cell Stem Cell, 3:301-313; Bell et al., (2010) Neuron, 68:409-427; Murray et al., (2014) Cell Mol Life Sci, 71:1353-1374) and therefore, the more vascularized the tissue is, the more rich the tissue is with MPCs. Nevertheless, the tissue source and the cells' derivation procedure can affect the abundance, phenotype and differentiation potency of MPCs (Baksh et al., (2007) Stem Cells, 25:1384-92; Heidari et al., (2013) Avicenna J Med Biotechnol, 5:104-117; Heo et al., (2016) Int J Mol Med, 37:115-125; Tan et al., (2012) Tissue Eng Part A, 18:840-851; De Bari et al., (2008) Arthritis Rheum, 58:240-250). Bone marrow (BM) has been one of the major sources of MPCs. However, the derivation of stem cells from patients and healthy donors is not always possible. Bone marrow extraction requires hospitalization and leads to considerable donor morbidity, including pain and bleeding, and other complication such as infection and risk for viral exposure (Buckner et al., (1984) Blood, 64:630-634; Nishimori et al., (2002) Blood, 99:1995-2001). Therefore, efforts have been made to find alternative sources of MPCs for cell therapies. Another current major source for MPC derivation is adipose tissue. However, 100 ml of tissue and blood collected from lipoaspiarates provides approximately $10^5$ cells (Francis et al., (2010) Organogenesis, 6:11-4). This is likely due to the mechanical trauma to the tissue incurred during the liposuction procedure, leading to a low yield and reduced cell viability (Zuk et al., (2002) Mol Biol Cell, 13:4279-4295). Yet, in order to achieve enough stem cells in the scale needed for clinical purposes, a large quantity of starting tissue material is needed which may result in considerable risk and donor morbidity.

Thus, there is a need in the art for methods for generating MPCs from an accessible source. The present invention addresses this need.

SUMMARY OF THE INVENTION

In one embodiment, the invention relates to an isolated tonsillar multipotent progenitor cell (T-MPC) or an isolated differentiated cell derived from a T-MPC.

In one embodiment, the differentiated cell is an osteoblast, a chondrocyte, an adipocyte, a smooth muscle cell or a neuron.

In one embodiment, the T-MPC is isolated from a tonsillar tissue. In one embodiment, the tonsillar tissue is from a palatine tonsil, a lingual tonsil, a pharyngeal tonsil, a tubal tonsil, a tonsillar crypt, or a Waldeyer's tonsillar ring. In one embodiment, the tonsillar tissue is from a palatine tonsil. In one embodiment, the tonsillar tissue is obtained from a biopsy of a tonsil. In one embodiment, the tonsillar tissue is from a human.

In one embodiment, the isolated T-MPC cell expresses at least one of CD44, CD90, CD73, CD105, TRA-1-80, and TRA-1-60.

In one embodiment, the invention relates to a pharmaceutical composition comprising at least one isolated tonsillar multipotent progenitor cell (T-MPC) or isolated differentiated cell derived from a T-MPC.

In one embodiment, the T-MPC cell is isolated from a tonsillar tissue from a palatine tonsil, a lingual tonsil, a pharyngeal tonsil, a tubal tonsil, a tonsillar crypt, or a Waldeyer's tonsillar ring. In one embodiment, the tonsillar tissue is from a palatine tonsil. In one embodiment, the tonsillar tissue is obtained from a biopsy of a tonsil. In one embodiment, the tonsillar tissue is from a human.

In one embodiment, the isolated cell is a T-MPC which expresses at least one of CD44, CD90, CD73, CD105, TRA-1-80, and TRA-1-60.

In one embodiment, the isolated cell is an osteoblast, chondrocyte, adipocyte, neuron or smooth muscle cell which is differentiated from a T-MPC.

In one embodiment, the invention relates to a method of isolating a T-MPC from a tonsillar tissue comprising the steps of: a) contacting a tonsillar tissue with a digestion solution comprising at least one collagenase enzyme; and b) separating the T-MPCs.

In one embodiment, the digestion solution comprises a combination of Collagenase I, Collagenase II and thermolysin. In one embodiment, the digestion solution further comprises a deoxyribonuclease.

In one embodiment, the method of separating the T-MPCs comprises the steps of centrifuging the cells and selecting cells having the lowest density.

In one embodiment, the method of separating comprises fluorescence-activated cell sorting. In one embodiment, the sorted cells express at least one of CD44, CD90, CD73, CD105, TRA-1-80 or TRA-1-60.

In one embodiment, the isolated T-MPCs are at least 80% pure, at least 85% pure, at least 90% pure, at least 95% pure, at least 97% pure, at least 98% pure, at least 99% pure, at least 99.5% pure, or at least 99.9% pure T-MPCs.

In one embodiment, the isolated T-MPCs are isolated from a tonsillar tissue sample of less than 2.0 cubic centimeters. In one embodiment, the tonsillar tissue sample is 1.0 cubic centimeters or less.

In one embodiment, the yield of T-MPCs is at least $2 \times 10^8$ cells per gram of tissue.

In one embodiment, the invention relates to a method of differentiating at least one T-MPC into at least one differentiated cell comprising the step of subjecting the at least one isolated T-MPC to conditions that promote differentiation into a differentiated cell selected from the group consisting of a smooth muscle cell, an osteoblast, a chondrocyte, an adipocyte, and a neuron.

In one embodiment, the conditions that promote differentiation comprise culturing the T-MPCs in the presence of differentiation medium.

In one embodiment, the differentiated cell is an osteoblast. In one embodiment, the differentiation medium is a medium allowing differentiation into osteoblasts.

In one embodiment, the differentiated cell is a chondrocyte. In one embodiment, the differentiation medium is a medium allowing differentiation into a chondrocyte.

In one embodiment, the differentiated cell is an adipocyte. In one embodiment, the differentiation medium is a medium allowing differentiation into an adipocyte.

In one embodiment, the invention relates to a method of treating disease or disorder in a subject comprising administering a therapeutically effective amount of a pharmaceutical composition comprising at least one isolated tonsillar multipotent progenitor cell (T-MPC) or isolated differentiated cell derived from a T-MPC to a subject in need thereof.

In one embodiment, the disease or disorder is one of blood and lymph conditions, cancers and other neoplasms, digestive system diseases, diseases and abnormalities at or before birth, ear, nose, and throat diseases, eye diseases, gland and hormone-related diseases, heart and blood diseases, immune system diseases, mouth and tooth diseases, muscle, bone, and cartilage diseases, nervous system diseases, nutritional and metabolic diseases, occupational diseases, respiratory tract (lung and bronchial) diseases, skin and connective tissue diseases, substance-related disorders, symptoms and general pathology, urinary tract, sex organ, and pregnancy-related conditions, viral diseases, or wounds and injuries.

In one embodiment, the invention relates to a kit comprising a container in which a pharmaceutical composition comprising at least one isolated tonsillar multipotent progenitor cell (T-MPC) or isolated differentiated cell derived from a T-MPC is contained.

In one embodiment, the container is a vial, tube, syringe or bag.

In one embodiment, the invention relates to a method of producing an implant, comprising applying at least one isolated T-MPC or isolated differentiated cell derived from a T-MPC to a biocompatible scaffold to produce a cell-seeded scaffold; and culturing the cell-seeded scaffold to allow the at least one isolated cell to divide and populate the biocompatible scaffold.

In one embodiment, the at least one isolated cell is a T-MPC, and the scaffold is subjected to conditions that promote differentiation of the at least one T-MPC into a differentiated cell selected from the group consisting of a smooth muscle cell, an osteoblast, a chondrocyte, an adipocyte, and a neuron.

In one embodiment, the invention relates to an implant produced by a method comprising applying at least one isolated T-MPC or isolated differentiated cell derived from a T-MPC to a biocompatible scaffold to produce a cell-seeded scaffold; and culturing the cell-seeded scaffold to allow the at least one isolated cell to divide and populate the biocompatible scaffold.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2, comprising FIG. 2A depicts exemplary experimental results demonstrating that an analysis of co-staining demonstrates that the T-MPCs are CD44 and CD90, CD73, and CD105 positive and CD19 and HLA-DR negative. n=14 donors in triplicates. Bm-MPC=bone marrow-derived mesenchymal progenitor cell, T-MPC=tonsillar mesenchymal progenitor cells. FIG. 2B depicts exemplary experimental results demonstrating that a fraction of the T-MPCs express the pluripotency related marker SSEA4. FIG. 2C depicts exemplary experimental results demonstrating that a fraction of the T-MPCs express the pluripotency related marker TRA-1-80. FIG. 2D depicts exemplary experimental results demonstrating that a fraction of the T-MPCs express the pluripotency related marker TRA-1-60.

FIG. 3, comprising FIG. 3A depicts exemplary experimental growth curves demonstrating cumulative population doubling (PD) per individual donors. Cells were split, counted, and $10^5$ T-MPCs were plated per cell split. FIG. 3B depicts exemplary experimental results demonstrating flow cytometry analyses with KI67 which marks dividing cells and the S-phase markers PCNA and BrdU show an actively dividing T-MPC population, which is comparable to bone marrow-derived MPCs (Bm-MPC). FIG. 3C depicts exemplary experimental growth curves demonstrating the population doublings of T-MPC lines in xeno-free medium: growth curves demonstrate cumulative PD in complete T-MPC medium (CM) containing bovine serum compared to cells grown in xeno-free medium (XFM). FIG. 3D depicts exemplary experimental growth curves demonstrating that the population doubling time in xeno-free medium ranges from 31 to 35 hours for at least four cell splits (20 days in culture).

FIG. 4, comprising FIG. 4A depicts exemplary experimental results demonstrating alizarin red S staining demonstrates calcium deposits in T-MPCs treated with osteogenic differentiation media (ODM). FIG. 4B depicts exemplary experimental results demonstrating undifferentiated T-MPCs grown in complete media (CM) are negative. FIG. 4C depicts exemplary experimental results demonstrating Real-time qPCR analysis validates the differentiation of T-MPCs in osteogenic media and shows a significant increase in expression of osteoblast markers compared to control. FIG. 4D depicts exemplary experimental results demonstrating real-time qPCR analysis validates the differentiation of T-MPCs in osteogenic media and shows a significant increase in expression of osteocyte markers compared to control. FIG. 4E depicts exemplary experimental results demonstrating Oil red O is negative in the control cells incubated at the same time and for the same duration in complete medium. FIG. 4F depicts exemplary experimental results demonstrating, oil droplets in T-MPCs differentiated in adipogenesis medium (ADM). FIG. 4G depicts exemplary experimental results demonstrating that real time RT-qPCR shows T-MPC-derived adipocytes express high levels of the adipogenic-specific genes PPRAG and Leptin compared to undifferentiated controls in CM. FIG. 4H depicts exemplary experimental results demonstrating alcian blue staining is negative in T-MPCs grown in CM. FIG. 4I depicts exemplary experimental results demonstrating T-MPC-derived chondrocytes grown in chondrogenesis media (CDM) stained in blue. FIG. 4J depicts exemplary experimental results demonstrating RT-qPCR confirms an increase in the chondrogenic-specific markers ACAN, COL10A1, and ATP2A2 following differentiation compared to undifferentiated T-MPC controls. All results are presented as mean±SEM obtained in triplicate from donors in multiple independent experiments. *$p \leq 0.05$, $p \leq 0.01$, *$p \leq 0.001$. ALP alkaline phosphatase, BMP2 bone morphogenetic protein 2, DMP1 dentin matrix protein 1, FGF23 fibroblast growth factor 23, MEPE matrix extracellular phospho-glycoprotein, OCN osteocalcin, OPN osteopontin, RUNX2 runt-related transcription factor 2, SOST sclerostin.

FIG. 5, comprising FIG. 5A depicts an exemplary schematic illustration of teratoma assay performed in NOD-SCID gamma (NSG) mice. Cells are subcutaneously injected into the fat pad. Following 7 months of monitoring the mice, no teratoma tumors were formed. Fat pad was harvested for whole-mount immunostaining. FIG. 5B depicts exemplary fluorescence microscope images of green fluorescent protein (GFP) and FIG. 5C depicts exemplary fluorescence microscope images of GFP combined with DAPI stain show MPC nuclei in the injected mouse fat pad. FIG. 5D depicts exemplary fluorescence microscope images of an immunostaining assay for the human-specific antibody HSP27 shows that cells are engrafted and survived for months after, but did not form a teratoma. FIG. 5E depicts the same image as FIG. 5D, with DAPI to demonstrate nuclei. White line indicates the grafted cells in the injection area.

DETAILED DESCRIPTION

Figure 1:
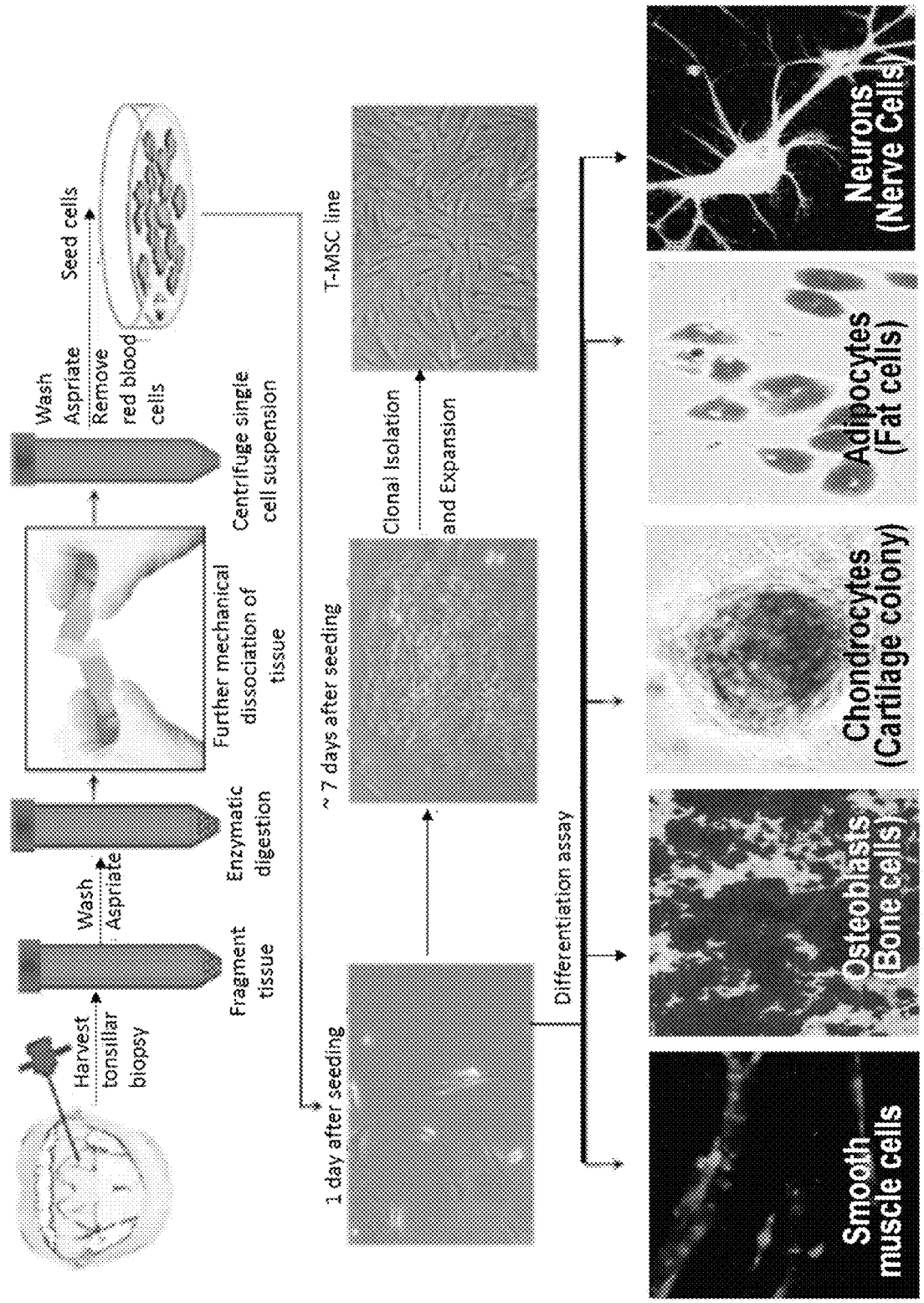
FIG. 1 depicts exemplary experimental results demonstrating a schematic workflow of tonsillar multipotent progenitor cell (T-MPC) isolation from human tonsillar biopsy. T-MPCs can be expanded in culture and differentiated into various lineages including: smooth muscle cells, osteoblasts (bone cells), chondrocytes (cartilage), adipocytes (fat cells) and neurons.

The present invention relates to the discovery of a method for isolating multipotent progenitor cells (MPCs) from small amounts of tonsillar tissue (T-MPCs) in a manner that retains the ability of the cells to proliferate and differentiate into multiple cell lineages including, but not limited to osteoblasts, chondrocytes, and adipocytes.

Described herein are methods of identifying and/or isolating T-MPCs. These T-MPCs can be distinguished by expression of cell surface markers such as CD44, CD90, CD73, CD105, TRA-1-80, and TRA-1-60.

Also described herein are therapeutic methods using the T-MPCs. In various embodiments, the T-MPCs or differentiated cells derived therefrom can be used to treat or prevent blood and lymph conditions, cancers and other neoplasms, digestive system diseases, diseases and abnormalities at or before birth, ear, nose, and throat diseases, eye diseases, gland and hormone-related diseases, heart and blood diseases, immune system diseases, mouth and tooth diseases, muscle, bone, and cartilage diseases, nervous system diseases, nutritional and metabolic diseases, occupational diseases, respiratory tract (lung and bronchial) diseases, skin and connective tissue diseases, substance-related disorders, symptoms and general pathology, urinary tract, sex organ, and pregnancy-related conditions, viral diseases, and wounds and injuries.

Definitions

Unless defined otherwise, all technical and scientific terms used herein have the same meaning as commonly understood by one of ordinary skill in the art to which the invention pertains. The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

The term "acceptable carrier" as used herein, means excipients, emollients, and stabilizers or stabilizing agents or other acceptable materials, compositions, or structures involved in holding, carrying, transporting, or delivering any subject cell or composition. Each means must be "acceptable" in the sense of being compatible with the other ingredients of a subject composition and not injurious to the subject.

As used herein, the term "autologous" is meant to refer to any material derived from the same individual to whom it is later to be re-introduced.

"Allogeneic" refers to any material derived from a different animal of the same species as the individual to whom the material is introduced. Two or more individuals are said to be allogeneic to one another when the genes at one or more loci are not identical. In some embodiments, allogeneic material from individuals of the same species may be sufficiently unlike genetically to interact antigenically.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, primary or metastatic melanoma, thymoma, lymphoma, sarcoma, lung cancer, liver cancer, non-Hodgkin lymphoma, Hodgkin lymphoma, leukemia, uterine cancer, cervical cancer, bladder cancer, kidney cancer and adenocarcinomas such as breast cancer, prostate cancer, ovarian cancer, pancreatic cancer, glioblastoma, neuroblastoma, and the like.

The term "derived from" refers to being generated, synthesized, or originating from a particular source, such that the derived matter is related to the source. The derived matter does not need to be identical to the particular source. In one embodiment, a cell is derived from a progenitor cell. In another embodiment, a cell is derived from a graft from a subject.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced into or produced outside an organism, cell, tissue or system.

The term "expand" as used herein refers to increasing in number, as in an increase in the number of cells. In one embodiment, the cells that are expanded ex vivo increase in number relative to the number originally present in the culture. In another embodiment, the cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene, and polypeptides obtained by translation of mRNA transcribed from a gene. In some embodiments, an expression product is transcribed from a sequence that does not encode a polypeptide, such as a microRNA.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell into which it is introduced.

The term "isolated cell" as used herein refers to a cell that has been removed from an organism in which it was originally found, or a descendant of such a cell. Optionally the cell has been cultured in vitro, e.g., in the presence of other cells. Optionally, the cell is later introduced into a second organism or re-introduced into the organism from which it (or the cell or population of cells from which it descended) was isolated.

The term "isolated population" with respect to an isolated population of cells as used herein refers to a population of cells that has been removed and separated from a mixed or heterogeneous population of cells. In some embodiments, an isolated population is a "substantially pure" population of cells as compared to the heterogeneous population from which the cells were isolated or enriched. In some embodiments, the isolated population is an isolated population of multipotent cells which comprise a substantially pure population of multipotent cells as compared to a heterogeneous population of somatic cells from which the multipotent cells were derived.

The terms "multipotent cell" or "progenitor cell" as used herein, refer to a cell in an undifferentiated or partially differentiated state that has the property of self-renewal and has the developmental potential to differentiate into multiple cell types. A progenitor cell is capable of proliferation and giving rise to more such progenitor cells while maintaining its developmental potential. Often, progenitor cells have significant or very high proliferative potential. Progenitor cells can give rise to multiple distinct cells having lower developmental potential, i.e., differentiated cell types, or to a single differentiated cell type, depending on the developmental pathway and on the environment in which the cells develop and differentiate. In theory, self-renewal can occur by either of two major mechanisms. Progenitor cells can divide asymmetrically, which is known as obligatory asymmetrical differentiation, with one daughter cell retaining the developmental potential of the parent progenitor cell and the other daughter cell expressing some distinct other specific function, phenotype and/or developmental potential from the parent cell. The daughter cells themselves can be induced to proliferate and produce progeny that subsequently differentiate into one or more mature cell types, while also retaining one or more cells with parental developmental potential. A differentiated cell may derive from a multipotent cell, which itself is derived from a multipotent cell, and so on. While each of these multipotent cells may be considered progenitor cells, the range of cell types each such progenitor cell can give rise to, i.e., their developmental potential, can vary considerably. Alternatively, some of the progenitor cells in a population can divide symmetrically into two progenitor cells, known as stochastic differentiation, thus maintaining some progenitor cells in the population as a whole, while other cells in the population give rise to differentiated progeny only. Accordingly, the term "progenitor cell" refers to any subset of cells that have the developmental potential, under particular circumstances, to differentiate to a more specialized or differentiated phenotype, and which retain the capacity, under certain circumstances, to proliferate without substantially differentiating. In some embodiments, the term progenitor cell refers generally to a naturally occurring parent cell whose descendants (progeny cells) specialize, often in different directions, by differentiation, e.g., by acquiring completely individual characters, as occurs in progressive diversification of cells and tissues. Some differentiated cells also have the capacity to give rise to cells of greater developmental potential. Such capacity may be natural or may be induced artificially upon treatment with various factors. Cells that begin as progenitor cells might proceed toward a differentiated phenotype, but then can be induced to "reverse" and re-express the progenitor cell phenotype, a term often referred to as "dedifferentiation" or "reprogramming" or "retrodifferentiation" by persons of ordinary skill in the art.

The term "differentiated cell" encompasses any somatic cell that is not pluripotent. Thus, the term a "differentiated cell" encompasses cells that are partially differentiated as well as cells that are terminally differentiated generated using any of the compositions and methods described herein. In some embodiments, the term "differentiated cell" also refers to a cell of a more specialized cell type (i.e., decreased developmental potential) derived from a cell of a less specialized cell type (i.e., increased developmental potential) where the cell has undergone a cellular differentiation process.

The term "tonsil" or "tonsillar tissue" as used herein includes the palatine tonsils, lingual tonsils, pharyngeal tonsils or nasopharyngeal tonsils (also called adenoids), tubal tonsils, the tonsillar crypts, and Waldeyer's tonsillar ring.

"Parenteral" administration of a composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a mammal in which a tonsillar tissue is present, including but not limited to a human, a dog, a cat, a mouse, a rat, a cow, a horse, a pig, a goat and a sheep.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The phrase "therapeutically effective amount," as used herein, refers to an amount that is sufficient or effective to prevent or treat (delay or prevent the onset of, prevent the progression of, inhibit, decrease or reverse) at least one sign or symptom of a disease or disorder, including alleviating at least one sign or symptom of a diseases or disorder.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses.

Ranges: throughout this disclosure, various embodiments of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

Provided herein are methods for isolating multipotent progenitor cells from tonsillar tissue (T-MPCs), compositions of matter comprising the isolated T-MPCs, and methods of use for the treatment of diseases.

Sources of T-MPCs

Prior to isolation, a source of T-MPCs may be obtained from a subject having a tonsillar tissue. Non-limiting examples of subjects include humans, dogs, cats, mice, rats, and transgenic species thereof. In one embodiment, the subject is a human. In one embodiment, the subject is a healthy subject. In one embodiment, the subject has been diagnosed with a disease or disorder.

T-MPCs can be obtained from a tonsillar tissue, including but not limited to, palatine tonsils, lingual tonsils, pharyngeal tonsils or nasopharyngeal tonsils (also called adenoids), tubal tonsils, the tonsillar crypts, and the Waldeyer's tonsillar ring. In one embodiment, the tonsillar tissue is a specimen from the palatine tonsils.

In various embodiments, the tonsillar tissue for use in the present invention may be a specimen taken as a biopsy or a specimen obtained following a surgical procedure (e.g., a tonsillectomy or adenoidectomy.) In one embodiment, the tonsillar tissue specimen is less than 2.0 cubic centimeters (cc), less than 1.5 cc, less than 1.0 cc, less than 0.9 cc, less than 0.8 cc, less than 0.7 cc, or less than 0.6 cc in size.

Isolation and Maintenance of Tonsillar Mesenchymal Progenitor Cells (T-MPCs)

In one embodiment, the tonsillar tissue is minced or micro-dissected into very small fragments. The purpose of mincing is to allow exposure of more cells to the digestion medium or to separate cells from each other. Non-limiting examples of methods that can be used to mince include devices that render mechanical shearing forces (i.e., homogenizer, mortar and pestle, blender, etc.), devices that render cuts or tears (i.e.m, scalpel, syringes, forceps, etc.), and ultrasonic devices.

In one embodiment, tonsillar tissues are treated to dissociate cells. In one embodiment, the method of dissociating tonsillar tissue uses an enzyme. Various enzyme treatments used to dissociate tissue are well known in the art. One method includes the use of at least one collagenase enzyme to digest partially sheared tonsillar tissue in a medium that will sustain viability of cells isolated from the tonsillar tissue. In one embodiment, the method uses a combination of two or more collagenase enzymes. At least one collagenase enzyme can be used in combination with at least one additional enzyme to digest the tonsillar tissue. Examples of other enzymes that could be used to digest tissue include neutral proteases, serine proteases including, but not limited to, trypsin, chymotrypsin, elastase, accutase, Liberase and thermolysin. In another embodiment, enzymes that digest nucleic acid molecules, including, but not limited to, a nuclease, a deoxyribonuclease, DNase I, RNase-free Deoxyribonuclease I, and RQ1 RNase-Free DNase, are used to cut the DNA into smaller pieces in order to prevent tissue aggregation by free DNA. In one embodiment, a combination of enzymes used to dissociate a tonsillar tissue is a combination of at least two of Collagenase I, Collagenase II, thermolysin and deoxyribonuclease. In one embodiment, the combination of Collagenase I, Collagenase II and thermolysin is formulated as a Liberase Enzyme Blend.

In one exemplary embodiment, tonsillar tissue is treated with about 1.6 U/ml of Liberase Enzyme Blend in combination with 100 μg/ml deoxyribonuclease. However, the amount of enzyme used for tonsillar tissue dissociation will depend on multiple factors including the enzyme formulation used and the size of the tonsillar tissue sample.

A wide variety of cell-sustaining media can be used to keep the pH of the liquid in a range that promotes survival of T-MPCs and to provide a sufficient volume of liquid within which the enzymatic digestion can occur. Non-limiting examples of such media include F12/DMEM, Ham's F10 (Sigma), CMRL-1066, Minimal essential medium (MEM, Sigma), RPMI-1640 (Sigma), Dulbecco's Modified Eagle's Medium (DMEM, Sigma), αMEM and Iscove's Modified Eagle's Medium (IMEM). In addition, any of the nutrient media described in Ham and Wallace Meth. Enz., 58:44 (1979), Barnes and Sato Anal. Biochem., 102:255 (1980), or Mather, J. P. and Roberts, P. E. "Introduction to Cell and Tissue Culture", Plenum Press, New York (1998) can also be used.

Dissociation treatment of tonsillar tissue with enzyme results in cell yields of various amounts. Some cells are in single cell suspensions, whereas others are in cell aggregates. Large cell aggregates can be separated from each other by repeating a mechanical or enzymatic separation method as detailed above.

In one embodiment, T-MPCs are separated from red blood cells (RBC) and cellular debris. Separating T-MPCs can be performed using any convenient method known in the art, for example, fluorescence-based sorting techniques and expression markers. Suitable expression markers include, but are not limited to cell surface markers whose expression is highly correlated with T-MPCs. One exemplary method of separating cells uses centrifugation. In such a method, centrifugation of the dissociated tonsillar cells results in the generation of a single pellet having the lower density T-MPCs in the upper portion of the pellet and the higher density RBCs in the lower portion of the pellet, and the upper portion of the pellet is collected. The amount of RBC and debris to be removed depends on several factors, such as the extent of digestion or mechanical shear forces applied to the tonsillar tissue. In some cases, one round of centrifugation and collection is sufficient to purify the T-MPCs. In other cases, more than one round of centrifugation and collection is required to purify the T-MPCs. The desired product is a population of relatively pure T-MPCs. In one embodiment, the isolated cell population of cells is at least 80% pure, at least 85% pure, at least 90% pure, at least 95% pure, at least 97% pure, at least 98% pure, at least 99% pure, at least 99.5% pure, or at least 99.9% pure T-MPCs.

An alternative method for isolating T-MPCs may utilize a density gradient. Compounds that can be used to create a density gradient include, but are not limited to, serum (i.e., bovine serum albumin or BSA), ovalbumin, nonionic synthetic polymers of sucrose (i.e., Ficoll™), colloidal polyvinylpyrrolidone-coated silica (i.e., Percoll™), polyvinylpyrrolidone (PVP), and methylcellulose. In a one embodiment, density gradients that are capable of neutralizing the enzymes used to digest tonsillar tissues are used. One example of such a density gradient is BSA. The amount of BSA used is about 50% volume-to-volume ratio, about 25%, about 10%, or about 5%.

Another alternative method of isolating T-MPCs may utilize positive or negative selection techniques. The T-MPCs can be enriched or depleted of cells expressing certain markers, including, but not limited to, CD44, CD90, CD73, CD105, TRA-1-80, TRA-1-60, CD19 and HLA-DR. Enrichment or depletion of these cells can be accomplished using an isolated antibody, a biological sample comprising an antibody (such as ascites), an antibody bound to a physical support, and a cell bound antibody. For example, enrichment of a T-MPC cell population by positive CD44+ selection can be accomplished using an antibody directed to CD44 or CD44-microbeads.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

Culturing T-MPCs

T-MPCs are then resuspended in a cell-sustaining media. The method of isolating T-MPCs of the present invention includes a proliferation step of culturing a T-MPC in the T-MPC culture medium of the present invention to allow the T-MPC to proliferate.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

A variety of cell-sustaining media is available for use. Examples include, but are not limited to, DMEM, IMEM, αMEM and RPMI-1640. For more optimal conditions to promote T-MPC survival and growth, a variety of nutrients may be added to supplement the media. Examples include, but are not limited to, insulin, transferrin, holo-transferrin, sodium pyruvate, L-alanyl-L-glutamine dipeptide, GlutaMax (200 mM L-alanyl-L-glutamine dipeptide in 0.85% NaCl), non-essential amino acids (NEAA), human serum albumin, BSA fraction V, fetal bovine serum (FBS), penicillin, streptomycin, KnockOut Serum Replacement, B-27 supplement, G-5 supplement, N-2 supplement, Smooth Muscle Growth Supplement (SMGS), and beta-mercaptoethanol. In one embodiment, the following amounts of nutrients are used to promote T-MPC survival and growth in a T-MPC medium: DMEM supplemented with at least 10% FBS; at least about 1% sodium pyruvate; at least about 1× GlutaMax; at least about 1% NEAA; at least about 1% penicillin/streptomycin; and at least about 100 µM beta-mercaptoethanol. In one embodiment, the FBS is heat inactivated.

In one embodiment, the cell-sustaining medium is a xenofree medium. In one embodiment, the following amounts of nutrients are used to promote T-MPC survival and growth in a xenofree medium: IMDM supplemented with at least about 100 µg/ml insulin; at least about 5 µg/ml transferrin; at least about 1 mM sodium pyruvate; at least about 2 mM GlutaMax; at least about 1% NEAA; and at least about 1 gr/100 ml human serum albumin or BSA fraction V.

Proliferation Step

The proliferation step according to the present invention may be performed under various conditions. In one embodiment, proliferation is performed under conditions of 30° C. to 40° C. and 2% to 8% CO2. In one embodiment, the proliferation step can be very short, for example less than 24 hours such as 1, 2, 3, 4, 5, 6, 7, 8, 9, 10, 11, 12, 13, 14, 15, 16, 17, 18, 19, 20, 21, 22, or 23 hours. In one embodiment, the proliferation step can be longer, for example 1, 2, 3, 4, 5, 6, 7, 8, 9, 10, 11, 12, 13, 14, or more days. During proliferation, replacement of the culture medium may be appropriately carried out by a known method.

The T-MPCs may be proliferated by the methods disclosed herein such that the original number of T-MPCs can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween.

In one embodiment, according to the method of producing T-MPCs of the present invention, the T-MPCs can proliferate to an amount allowing clinical use (e.g., $10^6$ to $10^7$ cells/mL or more).

The T-MPCs may be grown on different substrates. Non-limiting examples of substrates that may be used include fibronectin, laminin, collagen, polylysine, nitrocellulose, nylon, and polytetrafluoroethylene. In one embodiment, T-MPCs are grown on fibronectin-coated tissue culture plates in the nutrient media described above. In one embodiment, this culturing combination allows for growth of T-MPCs, but not of other cell types (e.g., T-lymphocytes and B-lymphocytes). The T-MPCs may then be subcultured and proliferated or collected and cryopreserved as desired. Subculturing T-MPCs to obtain a greater number of cells is accomplished by taking T-MPCs and dividing the plurality of cells into multiple tissue culture containers. Nutrient media is then added to each of the tissue culture containers to achieve a lower concentration of T-MPCs than in the original tissue culture container. When subculturing of T-MPCs is desired, the adherent T-MPCs can be dissociated from the tissue culture container using accutase prior to confluence. In one exemplary embodiment, the T-MPCs are dissociated when they reach about 70% confluence and are subcultured at a density of at least about $5 \times 10^6$ cells per 10 cm plate.

In one embodiment, T-MPCs may be fed by replacing the entirety of the old nutrient media with new nutrient media. In various embodiments, the frequency of feeding for promoting the survival and growth of T-MPCs is at least once a week, at least twice a week, at least three times a week, once a day or every other day.

In one embodiment, T-MPCs may be fed with conditioned media in which these cells were grown. Because the T-MPCs described herein are unique to this invention and will secrete factors specific to these cells, the conditioned media derived from the T-MPCs are also unique. Addition of conditioned media may be used to promote greater vitality in the T-MPCs. In various embodiments, T-MPCs may be fed with conditioned media at a concentration of at least about 1% to at least about 25% of total media volume.

The nutrient media that is added may be dependent on whether differentiation of the T-MPCs desired. The T-MPCs of this invention can be passaged multiple times while retaining dividing capability and without inducing differentiation of these T-MPCs into terminally differentiated cells. When maintenance of the T-MPCs is desired, the nutrient media that is added may be T-MPC medium or a xenofree medium. When differentiation of T-MPCs is desired, the nutrient media that is added may be a differentiation medium as described in detail elsewhere herein.

Following proliferation, or culturing, the T-MPCs are harvested from the culture apparatus whereupon the T-MPCs can be used immediately or cryopreserved to be stored for later use. In one embodiment, the invention includes cryopreserving the expanded T-MPCs. The cryopreserved, expanded T-MPCs are then thawed prior to further use (e.g., culturing for further use in any appropriate assay or differentiation). While many freezing solutions and parameters are known in the art and will be useful in this context, in a non-limiting example, one method involves using 10% DMSO in FBS, HypoThermosol, Viaspan or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

Differentiation of T-MPCs

In various embodiments, the invention relates to cells that result from the differentiation of a T-MPC of the invention. In one embodiment, the T-MPCs of the invention may differentiate into cells including, but not limited to, smooth muscle cells, osteoblasts (bone cells), chondrocytes (cartilage), adipocytes (fat cells) and neurons. Therefore, in one embodiment, the invention provides a population of differentiated cells derived from a T-MPC of the invention. In one embodiment, the invention provides a population of smooth muscle cells, osteoblasts, chondrocytes, adipocytes, or neurons derived from a T-MPC of the invention.

Methods of differentiating a T-MPC into different cell types include culturing a T-MPC in a culture medium for differentiation of the specific desired cell type.

Differentiation of T-MPCs into the osteogenic lineage may be achieved by culture in osteogenic medium. For example, T-MPCs may be cultured in T-MPC medium before changing to a medium that allows osteogenic differentiation. Medium that allows osteogenic differentiation is generally known in the art. In one embodiment, the following medium allows osteogenic differentiation: phenol red free DMEM supplemented with antibiotics, for example 100 U/ml of penicillin, 100 µg/ml of streptomycin, 0.1 µM to 10 nM dexamethasone, 0.15 mM to 50 µg/ml L-ascorbic acid 2-phosphate, 10 mM β-glycerophosphate and 10% Fetal Bovine Serum.

Differentiation of T-MPCs into the chondrogenic lineage in certain embodiments may be achieved by culture in chrondrogenic medium. For example, T-MPCs may be cultured in T-MPC medium before changing to a medium that allows chondrogenic differentiation. Medium that allows chondrogenic differentiation is generally known in the art and includes but is not limited to, DMEM supplemented with Cambrex chondrogenic single aliquots or StemPro® Osteocyte/Chondrocyte Differentiation Basal Medium with a StemPro® Chondrogenesis Supplement. In one embodiment, the following medium allows chondrogenic differentiation: phenol red free DMEM supplemented with, sodium pyruvate, Glutamax, 100 nM dexamethasone, 50 µg/mL ascorbic acid-2-phosphate, 100 µg/mL sodium pyruvate, 40 µg/mL L-proline, 10 ng/mL recombinant human transforming growth factor-β3 and 50 mg/mL insulin-transferrin-selenium (ITS)-premix stock. The cells can be cultured as spheres in suspension, on ultralow attachment plates or can be concentrated and cultured in droplets in tissue culture treated plates.

Differentiation of T-MPCs into the adipogenic lineage in certain embodiments may be achieved by culture in adipogenic medium. For example, T-MPCs may be cultured in T-MPC medium before changing to a medium that allows adipogenic differentiation. Medium that allows adipogenic differentiation is generally known in the art and includes, but is not limited to MesenCult™ Adipogenic Differentiation Medium and StemPro Adipogenesis Differentiation medium. In one embodiment, the following medium allows adipogenic differentiation: phenol red free DMEM, supplemented with 10% Fetal Bovine Serum, 3-isobutyl-1-methylxanthine (0.5 mM), Dexamethasone (10 µM), Insulin (10 µg/ml), and 1% penicillin/streptomycin. In an alternative embodiment, DMEM medium/Ham's F12 (vol/vol, 1:1), supplemented with antibiotics, for example 100 U/ml of penicillin, 100 µg/ml of streptomycin, 5 µg/ml human insulin, 10 µg/ml of human transferrin, PPARγ activator, for example 1 µM of BRL49653, or 2 µm of Ciglitazone (Biomol), 100 to 250 µM of isobutyl-methylxanthine (IBMX), 1 µM of dexamethasone, and 0.2 nM of triiodothyronin. 48 to 72 hours later, this medium is replaced by the same medium containing no IBMX or dexamethasone.

Characterization of T-MPCs

The population of T-MPCs of this invention isolated in the manner disclosed herein have several defining characteristics. First, the T-MPCs are at a stage that can be described as "non-terminally differentiated." The T-MPCs of this invention have the capacity to differentiate into one of multiple different lineages. In various embodiments, the T-MPCs of the invention are able to differentiate into osteogenic, chondrogenic, adipogenic, neural, or muscle lineages.

Cell-sustaining media or the nutrient media disclosed herein or conditioned media may be used to culture the T-MPCs in vitro. T-MPCs of this invention have the capacity to be passaged multiple times in the nutrient media disclosed herein. In one embodiment, T-MPCs of this invention are maintained at their pre-existing pre-differentiation state for at least 1, 2, 3, 4, 5, 6, 7, 8, 9, 10, 11, 12, 13, 14, 15, 16, 17, 18, 19, 20, 21, 22, 23, 24, 25 or more than 25 passages. Differentiation potential is retained during each passage and at any point after each passage T-MPCs of this invention can differentiate into functional osteogenic, chondrogenic, or adipogenic lineages cells.

At any point after each passage, T-MPCs may be used as an immunogen, for cell therapy, for bioassays, to establish a human cell line, or for drug discovery and/or development as disclosed herein. In one embodiment, the T-MPCs of this invention have the capacity to differentiate into functional osteogenic, chondrogenic, or adipogenic lineages cells upon transplantation into a recipient mammal.

Identification of T-MPCs may be accomplished by specific markers. Markers that can be used to detect T-MPCs include both positive (expressed) and negative (unexpressed) markers. Exemplary positive markers that may be used to identify T-MPCs include, but are not limited to, CD44, CD90, CD73, CD105, TRA-1-80, and TRA-1-60. Exemplary negative markers that may be used to identify T-MPCs include CD19, CD45, CD31 and HLA-DR. Therefore, in one embodiment, the T-MPCs of the invention are CD44, CD90, CD73, and CD105 positive and CD19, CD45, CD31 and HLA-DR negative.

Engineered T-MPCs

In some embodiments, T-MPCs or cells derived therefrom are transfected with genetic material prior to use in the methods of the invention. Useful genetic material includes, for example, transgenes which can be expressed to provide an additional function or restore a normal function to the cells or genetic sequences which are capable of reducing or eliminating an immune response in a host. For example, the expression of cell surface molecules, such as class I and class II histocompatibility antigens, may be suppressed. In some embodiments, this allows the transplanted cells to have reduced chance of rejection by the host.

In some embodiments, methods for genetically engineering cells with retroviral vectors, polyethylene glycol, or other methods known to those skilled in the art are used. These include using expression vectors which transport and express nucleic acid molecules in the cells. (See Goeddel; Gene Expression Technology: Methods in Enzymology 185, Academic Press, San Diego, Calif. (1990)).

Vector DNA is introduced into cells via conventional transformation or transfection techniques. Suitable methods for transforming or transfecting host cells can be found in Sambrook et al. (Molecular Cloning: A Laboratory Manual, 3nd Edition, Cold Spring Harbor Laboratory press (2001)), and other laboratory textbooks.

In addition to the above-described methods for inserting functional DNA transgenes into donor cells, other methods may be used. For example, non-vector methods include nonviral physical transfection of DNA into cells. In various embodiment, nonviral methods include, but are not limited to, microinjection (DePamphilis et al., Biotechnique 6:662-680 (1988)); electroporation (Toneguzzo et al., Molec. Cell. Biol. 6:703-706 (1986), Potter, Anal. Biochem. 174:361-373 (1988)); chemically mediated transfection such as calcium phosphate transfection (Graham and van der EB, supra, Chen and Okayama, Mol. Cell. Biol. 7:2745-2752 (1987), Chen and Okayama, Biotechnique, 6:632-638 (1988)) and DEAE-dextran mediated transfer (McCutchan and Pagano, J. Natl. Cancer Inst. 41:351-357 (1968)); cationic liposomal mediated transfection (Feigner et al., Proc. Natl. Acad. Sci. USA, 84:7413-7417 (1987), Feigner and Holm, Focus 11:21-25 (1989) and Feigner et al., Proc. West. Pharmacol. Soc., 32: 115-121 (1989)) and other methods known in the art.

Methods of Using T-MPCs

Bioassays

The T-MPCs disclosed herein can be used in various bioassays. In one embodiment, the T-MPCs are used to determine which biological factors are required for differentiation. By using the T-MPCs in a stepwise fashion in combination with different biological compounds (such as hormones, specific growth factors, etc.), one or more specific biological compounds can be found to induce differentiation into various lineages. Other uses in a bioassay for T-MPCs are differential display (i.e., mRNA differential display) and protein-protein interactions using secreted proteins from T-MPCs. Protein-protein interactions can be determined with techniques such as the yeast two-hybrid system. Proteins from T-MPCs can be used to identify other unknown proteins or other cell types that interact with T-MPCs. These unknown proteins may be one or more of the following: growth factors, hormones, enzymes, transcription factors, translational factors, and tumor suppressors. Bioassays involving T-MPCs and the protein-protein interaction these cells form and the effects of protein-protein or even cell-cell contact may be used to determine how surrounding tissue, such as mesenchymal tissue, contributes to T-MPC differentiation.

Drug Discovery

In some embodiments, the present invention provides methods for screening for therapeutic agents that may regulate the growth, regeneration, function and/or differentiation of T-MPCs. In some embodiments, the present invention can be used to screen for molecules with potential therapeutic effects. The T-MPC population may secrete proteins that have not been heretofore discovered or characterized. Proteins secreted by T-MPCs may be used as targets for drug development. In one embodiment, drugs can be made to target specific proteins on T-MPCs in vivo. Binding of the drug may promote differentiation or dedifferentiation of the T-MPCs. This approach may be useful, for example, to generate human tissue for cell therapy or tissue transplantation or to generate a population of dedifferentiated multipotent cells. In another embodiment, a drug may be an inhibitor of the growth of progenitor cells or cancer cells which express T-MPC markers. Any T-MPC marker can be used as a target to develop therapeutic antibodies, proteins, or small molecule drugs.

Therapy

In one embodiment, the T-MPCs cells, or cells derived therefrom, as described herein may be included in a composition for therapy. The therapeutic composition of the invention can be administered to an animal, such as a mammal, for example, a human, to treat a disease or disorder. Exemplary diseases and disorders that can be treated using the T-MPCs or differentiated cells derived therefrom include, but are not limited to, blood and lymph conditions, cancers and other neoplasms, digestive system diseases, diseases and abnormalities at or before birth, ear, nose, and throat diseases, eye diseases, gland and hormone-related diseases, heart and blood diseases, immune system diseases, mouth and tooth diseases, muscle, bone, and cartilage diseases, nervous system diseases, nutritional and metabolic diseases, occupational diseases, respiratory tract (lung and bronchial) diseases, skin and connective tissue diseases, substance-related disorders, symptoms and general pathology, urinary tract, sex organ, and pregnancy-related conditions, viral diseases, and wounds and injuries.

In various embodiments, the T-MPCs or differentiated cells derived therefrom can be used to treat at least one of the following diseases and disorders: Ulcerative Colitis, Diabetes Mellitus, Type 1, Liver Cirrhosis, Nonunion Fractures, Diabetic Foot, Critical Limb Ischemia, Dilated Cardiomyopathy, Autoimmune Diseases; Immune System Diseases; Demyelinating Diseases; Nervous System Diseases; Demyelinating Autoimmune Diseases, CNS; Autoimmune Diseases of the Nervous System (MS), Sjogren's Syndrome, Graft Versus Host Disease; Chronic and Expanded Graft Versus Host Disease, Middle Cerebral Artery Infarction, Osteoarthritis, Aplastic Anemia, Maxillary Cyst; Bone Loss of Substance, Spinal Cord Injury, Parkinson's Disease, Crohn's Disease, Acute Myocardial Infarction, Multiple Sclerosis, Hematological Malignancies, Organ Transplantation, Ischemia; Stroke, Systemic Sclerosis, Hereditary Ataxia, Liver Failure, Retinitis Pigmentosa, Kidney Transplant; Rheumatoid Arthritis, Lumbar Spondylolisthesis Involving L4-L5, Chronic Allograft Nephropathy, Degenerative Arthritis; Chondral Defects; Osteochondral Defects, Progressive Multiple Sclerosis; Neuromyelitis Optica, Primary Biliary Cirrhosis, Osteonecrosis of the Femoral Head, Pened Chest Surgery for Programmes Coronary Bypass, Lupus Nephritis, Wilson's Disease, Multiple System Atrophy, Burns, Intervertebral Disc Disease, Chronic Myocardial Ischemia; Left Ventricular Dysfunction, Relapsing-Remitting Multiple Sclerosis; Secondary Progressive Multiple Sclerosis; Progressive Relapsing Multiple Sclerosis, Tibial Fracture, Bone Cyst, Buerger's Disease, Amyotrophic Lateral Sclerosis, Allogeneic Stem Cell Transplantation, Idiopathic Pulmonary Fibrosis, Type 2 Diabetes Mellitus, Refractory Systemic Lupus Erythematosus, Leukemia, Myeloid, Acute; Leukemia, Lymphoblastic, Acute; Leukemia, Myelocytic, Chronic; Myeloproliferative Disorders; Myelodysplastic Syndromes; Multiple Myeloma; Leukemia, Lymphocytic, Chronic; Hodgkin's Disease; Lymphoma, Non-Hodgkin, Degenerative Arthritis, Myelodysplastic Syndrome, ST-Elevation Myocardial Infarction, Pulmonary Disease, Chronic Obstructive; Pulmonary Emphysema; Chronic Bronchitis, Lower Back Pain; Disc Degeneration, Articular Cartilage Lesion of the Femoral Condyle, Osteoporotic Fractures, Bone Neoplasms, Solid Tumors; Acute Kidney Injury, Hereditary Cerebellar Ataxia, Primary Disease, Autism, Limbus Corneae Insufficiency Syndrome, Wound Healing, Dementia of the Alzheimer's Type, Non-ischemic Dilated Cardiomyopathy, Stroke, Epidermolysis Bullosa, Tibia or Femur Pseudo-arthrosis, Recovery Following Partial Medial Meniscectomy, Human Immunodeficiency Virus, Stable Angina; Heart Failure; Atherosclerosis; Multivessel Coronary Artery Disease, Osteogenesis Imperfecta, Emphysema, Progressive Hemifacial Atrophy; Romberg's Disease, Complex Perianal Fistula, Multiple Trauma, Osteodysplasia, Tibiotalar Arthrodesis; Subtalar Arthrodesis; Calcaneocuboid Arthrodesis; Talonavicular Arthrodesis; Double Arthrodesis (i.e., Calcaneocuboid and Talonavicular); Triple Arthrodesis (i.e. Subtalar, Calcaneocuboid, and Talonavicular), Recto-vaginal Fistula, Peripheral Vascular Diseases, Prostate Cancer; Erectile Dysfunction, Diabetic Wounds; Venous Stasis Wounds, Ovarian Cancer; Sarcoma; and Small Intestine Cancer.

In certain embodiments, T-MPCs are administered to treat diseases, disorders or injuries of the bone or cartilage. As an example, a subject in need may have damage to a tissue, such as bone tissue, and the method provides an increase in biological function of the tissue by at least 5%, 10%, 25%, 50%, 75%, 90%, 100%, or 200%, or even by as much as 300%, 400%, or 500%. As yet another example, the subject in need may have a disease, disorder, or condition, and the method provides an administration of T-MPCs or compositions comprising them, sufficient to ameliorate or stabilize the disease, disorder, or condition. For example, the subject may have a disease, disorder, or condition that results in the loss, atrophy, dysfunction, or death of bone and/or cartilage cells. Exemplary treated diseases and disorders include arthritis; osteoarthritis; osteoporosis; osteochondrosis; osteochondritis; osteogenesis imperfecta; osteomyelitis; osteophytes (i.e., bone spurs); achondroplasia; costochondritis; chondroma; chondrosarcoma; herniated disk; Klippel-Feil syndrome; osteitis deformans; osteitis fibrosa cystica, a congenital defect that results in the absence of a tissue; accidental tissue defect or damage such as fracture, wound, or joint trauma; an autoimmune disorder; diabetes (e.g., Charcot foot); cancer; a disease, disorder, or condition that requires the removal of a tissue (e.g., tumor resection); periodontal disease; and implant extraction. In a further example, the subject in need may have an increased risk of developing a disease, disorder, or condition that is delayed or prevented by the method.

The methods, compositions, and devices of the application can include concurrent or sequential treatment with one or more of enzymes, ions, growth factors, and biologic agents, such as thrombin and calcium, or combinations thereof. The methods, compositions, and devices of the application can include concurrent or sequential treatment with non-biologic or biologic drugs.

In one embodiment, T-MPCs are cultured to obtain sufficient numbers of T-MPCs for transplantation or administration to a recipient. In various embodiments, T-MPCs are grown under standard incubation conditions for at least half a day, at least 1 day, at least 2 days, at least 3 days, at least 4 days, at least 5 days, at least 6 days, at least 7 days, or more than 7 days prior to administration. In one embodiment, T-MPCs are administered to a recipient and allowed to differentiate after administration. In another embodiment, T-MPCs are allowed to differentiate prior to administration to a recipient.

In one embodiment, the T-MPCs, or differentiated cells derived therefrom, are administered to the same subject from which they were isolated (i.e., the T-MPCs, or differentiated cells derived therefrom are autologous to the recipient.) Alternatively, the T-MPCs, or differentiated cells derived therefrom, are administered to a different recipient subject than the subject from which they were isolated. Therefore, in various embodiments, the T-MPCs, or differentiated cells derived therefrom are allogenic, or xenogenic to the recipient.

Pharmaceutical Compositions

For the administration in the prevention and/or treatment of a disease or disorder, T-MPCs of the invention can be formulated in a suitable composition, comprising T-MPCs of the invention, in a therapeutically or prophylactically effective amount, together with a suitable pharmaceutically acceptable vehicle. The composition of the invention can be formulated according to the chosen form of administration. For example, a composition is prepared in a liquid dosage form, e.g., as a suspension, to be injected into the subject in need of treatment. The composition of the invention can contain a prophylactically or therapeutically effective amount of the cells of the invention, optionally in a substantially purified form, together with the suitable vehicle in the appropriate amount in order to provide the form for proper administration to the subject. Suitable carriers or components typically used alone, or in combination, are known in the art and include, but are not limited to, water, saline, dextrose, and glycerol.

The compositions of the invention, if desired, can also contain, when necessary, additives to enhance, control, or otherwise direct the intended therapeutic effect of the cells comprising said pharmaceutical composition, and/or auxiliary substances or pharmaceutically acceptable substances, such as minor amounts of pH buffering agents, tensioactives, co-solvents, preservatives, etc. For example, the pharmaceutical composition comprises constituents which protect, culture, and maintain the T-MPCs for a desired treatment period (for example at least 1 day, 2 days, 3 days, 4 days, 5 days, 6 days, 1 week, 2 weeks or more than 2 weeks) thereby extending the release of therapeutic extracellular factors from the encapsulated cells. The pharmaceutical composition can also contain constituents to maintain the T-MPCs in undifferentiated form. The stability of the cells in the pharmaceutical composition of the invention can be improved by means of adding additional substances, such as, for example, amino acids such as aspartic acid, glutamic acid, etc. Pharmaceutically acceptable substances that can be used in the pharmaceutical composition of the invention are known, in general, by the skilled person in the art and are normally used in the manufacture of cellular compositions.

The compositions may also include auxiliary substances such as growth factors, cytokines, hormones, and various nutrients. Illustrative growth factors may include transforming growth factor-beta (TGF-beta.), fibroblast growth factors (FGFs), insulin like growth factors (IGFs), bone morphogenic proteins (BMPs); illustrative cytokines may include cytokine-like 1 (Cytl1); illustrative hormones may include human growth hormone (HGH); and testosterone; and illustrative nutrients may include ascorbic acid, pyruvate, hyaluronic acid and amino acids.

The compositions may also include additional therapeutic agents routinely used in the art. Exemplary additional therapeutic agents include, but are not limited to agents for alleviation of pain and inflammation such as narcotics, corticosteroids, anti-inflammatories including ibuprofen, naproxen, diclofenac, antibiotics, analgesics, and natural remedies.

Pharmaceutical compositions of the present invention may comprise a T-MPC population as described herein, or a population of cells derived from a T-MPC of the invention, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In one embodiment, compositions of the present invention are formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

It can generally be stated that a pharmaceutical composition comprising the T-MPCs, cells derived therefrom, or a compound identified in a screen of the invention, described herein may be administered at a dosage of $10^2$ to $10^9$ cells/kg body weight, including all integer values within those ranges. The cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments of the present invention, cells expanded using the methods described herein or a compound identified in a screen of the invention, are administered to a patient in conjunction with (e.g., before, simultaneously or following) any number of relevant treatment modalities, including but not limited to treatment with agents such as antiviral therapy, chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by T-MPC transplantation. In certain embodiments, following the transplant, subjects receive an infusion of the expanded immune cells of the present invention. In an additional embodiment, T-MPCs are administered before or following surgery.

The dosage of the above treatments to be administered to a patient will vary with the precise nature of the condition being treated and the recipient of the treatment. The scaling of dosages for human administration can be performed according to art-accepted practices.

In one example of a therapeutic composition, T-MPCs are produced by any of the methods described herein. T-MPCs are then prepared for application to subjects in need of the cells. T-MPCs can also be prepared in pharmaceutical dosages (e.g., in a pharmaceutically acceptable solution) and stored in appropriate containers. The T-MPCs can be stored in an appropriate manner (e.g., frozen) until needed. Additionally, the pharmaceutical dosages can be placed in pre-prepared syringes, catheters or other medical devices appropriate for delivery to a subject in need thereof. One of skill in the art will recognize that dosage amount and other such parameters can be adjusted for any individual preparation.

A pharmaceutical composition containing T-MPCs of the present invention may be stored until use by means of conventional methods known by the skilled person in the art. For short term storage (less than 6 hours) the pharmaceutical composition containing said cells may be stored at or below room temperature in a sealed container with or without supplementation with a nutrient solution. In some embodiments, medium-term storage (less than 48 hours) is performed at 2-8° C., with the pharmaceutical composition comprising an iso-osmotic, buffered solution in a container composed of or coated with a material that prevents cell adhesion. In some embodiments, longer term storage is performed by appropriate cryopreservation and storage under conditions that promote retention of cellular function.

T-MPCs produced, stored, or banked may be administered to non-autologous recipients in either prepared dosages or pre-dosage containers and can be shipped to medical facilities through any approved delivery system (governmentally approved and/or commercial). T-MPCs can be delivered directly from the manufacturer or via an intermediary.

Administration of Therapeutic Compositions

The administration of the therapeutic composition of the invention may be carried out in any convenient manner known to those of skill in the art. The therapeutic composition of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the therapeutic compositions of the invention are injected directly into a site of inflammation in the subject, a local disease site in the subject, a lymph node, an organ, a tumor, and the like.

The administration of the therapeutic composition of the invention to the subject in need thereof can be carried out by conventional means. In a particular embodiment, said therapeutic composition can be administered to the subject in need by administration using devices such as syringes, catheters, trocars, cannulae, etc. for direct injection into a joint to help repair cartilage, injection into subchondral defects, bone fractures, etc. engineering various cell-based scaffolds for implantation for bone or cartilage repair, or bone paste materials. In any case, the pharmaceutical composition of the invention will be administered using the appropriate equipment, apparatus, and devices which are known by the skilled person in art in a therapeutically or prophylactically effective amount, together with a suitable pharmaceutically acceptable vehicle.

T-MPCs disclosed herein can be applied by several routes including direct injection into the affected anatomical site. A therapeutic composition containing the cells may be injected in a single bolus, through a slow infusion, or through a staggered series of applications separated by several hours, several days or weeks. In any case, the therapeutic composition of the invention will be administered to the target tissue using the appropriate equipment, apparatus, and devices which are known by the skilled person in art in a therapeutically or prophylactically effective amount.

One of skill in the art will recognize that cell numbers (e.g., dosage amount) will vary depending upon multiple factors including, but not limited to site of administration, extent of disease, and method of administration. For example, an administration via local injection to a specific site or tissue will typically contain a smaller number of cells than an administration of the cells into the bloodstream. The dose of cells disclosed herein can be repeated, depending on the patient's condition and reaction, at time intervals of days, weeks or months as determined necessary by a treating physician or other healthcare professional.

The actual amount of T-MPCs administered, and rate and time-course of administration, will depend on the nature and severity of the disease or disorder being treated. Prescription of treatment, e.g. decisions on dosage etc., is within the responsibility of general practitioners and other medical doctors, and will typically take account of the nature of the disease or disorder, the condition of the individual patient, the site of delivery, the method of administration and other factors known to practitioners. Single or multiple administrations of T-MPCs doses may be administered in accordance with the guidance of the prescribing medical practitioner. Purely by way of example, T-MPCs may be delivered in dosages of about 10-10,000,000 cells. Examples of the techniques and protocols mentioned above can be found in Remington's Pharmaceutical Sciences, 20th Edition, 2000, pub. Lippincott, Williams & Wilkins.

Cells of the invention, or cells derived therefrom, can be administered in dosages and routes and at times to be determined in appropriate pre-clinical and clinical experimentation and trials. Cell compositions may be administered multiple times at dosages within these ranges. Administration of the cells of the invention may be combined with other methods useful to treat the desired disease or condition as determined by those of skill in the art.

The therapeutic compositions described herein can also be administered using any number of matrices. Therapeutic compositions and medicaments of the invention may take the form of a biomaterial that is coated and/or impregnated with T-MPCs, or differentiated cells derived therefrom. In one embodiment, an implant may be formed from the biomaterial and be surgically implanted to assist in bone, cartilage or tissue growth, regeneration, restructuring and/or re-modeling. Accordingly, the present invention can utilize those matrix compositions and formulations which have demonstrated utility in tissue engineering. Accordingly, the type of matrix that may be used in the compositions, devices and methods of the invention is virtually limitless and may include both biological and synthetic matrices. In one particular example, the compositions and devices set forth by U.S. Pat. Nos. 5,980,889; 5,913,998; 5,902,745; 5,843,069; 5,787,900; or 5,626,561 are utilized, as such these patents are incorporated herein by reference in their entirety. Matrices comprise features commonly associated with being biocompatible when administered to a mammalian host. Matrices may be formed from natural and/or synthetic materials. The matrices may be non-biodegradable in instances where it is desirable to leave permanent structures or removable structures in the body of an animal, such as an implant; or biodegradable. The matrices may take the form of sponges, implants, tubes, telfa pads, fibers, hollow fibers, lyophilized components, gels, hydrogels, powders, porous compositions, or nanoparticles. In addition, matrices can be designed to allow for sustained release of seeded cells or produced cytokine or other active agent. In certain embodiments, the matrix of the present invention is flexible and elastic, and may be described as a semisolid scaffold that is permeable to substances such as inorganic salts, aqueous fluids and dissolved gaseous agents including oxygen.

The biomaterial may be suitable for implantation in tissue, or may be suitable for administration (e.g. as microcapsules in solution). The implant should be biocompatible, e.g. non-toxic and of low, or no, immunogenicity. The biomaterial may be biodegradable such that the biomaterial degrades as wound healing occurs, ultimately leaving only the regenerated tissue in situ in the subject. Alternatively a non-biodegradable biomaterial may be used, e.g. to guide bone regeneration over a large discontinuity and/or to act as a structural support during bone healing, with surgical removal of the biomaterial being an optional requirement after successful wound healing.

The matrix configuration can be dependent on the tissue that is to be produced. In some embodiments, the matrix is a pliable, biocompatible, porous template that allows for target tissue growth. The matrix can be fabricated into structural supports, where the geometry of the structure is tailored to the application. The porosity of the matrix is a design parameter that influences cell introduction or cell infiltration. The matrix can be designed to incorporate extracellular matrix proteins that influence cell adhesion and migration in the matrix. Biomaterials may be soft and/or flexible, e.g. hydrogels, fibrin web or mesh, or collagen sponges. A "hydrogel" is a substance formed when an organic polymer, which can be natural or synthetic, is set or solidified to create a three-dimensional open-lattice structure that entraps molecules of water or other solutions to form a gel. Solidification can occur by aggregation, coagulation, hydrophobic interactions or cross-linking Alternatively biomaterials may be relatively rigid structures, e.g. formed from solid materials such as plastics or biologically inert metals such as titanium. The biomaterial may have a porous matrix structure which may be provided by a cross-linked polymer. In some embodiments, the matrix is permeable to nutrients and growth factors required for tissue growth.

Matrix structures may be formed by crosslinking fibers, e.g. fibrin or collagen, or of liquid films of sodium alginate, chitosan, or other polysaccharides with suitable crosslinkers, e.g. calcium salts, polyacrylic acid, heparin. Alternatively, scaffolds may be formed as a gel, fabricated by collagen or alginates, crosslinked using well established methods known to those skilled in the art.

Suitable polymer materials for matrix formation include, but are not limited to, biodegradable/bioresorbable polymers which may be chosen from the group of: agarose, collagen, fibrin, chitosan, polycaprolactone, poly(DL-lactide-co-caprolactone), poly(L-lactide-co-caprolactone-co-glycolide), polyglycolide, polylactide, polyhydroxyalcanoates, co-polymers thereof, or non-biodegradable polymers which may be chosen from the group of: cellulose acetate; cellulose butyrate, alginate, polysulfone, polyurethane, polyacrylonitrile, sulfonated polysulfone, polyamide, polyacrylonitrile, polymethylmethacrylate, co-polymers thereof.

A matrix with a high porosity and an adequate pore size can provide for increased cell introduction and diffusion throughout the whole structure of both cells and nutrients. Matrix biodegradability can provide for absorption of the matrix by the surrounding tissues (e.g., after differentiation and growth of tissues from progenitor cells) and can eliminate the necessity of a surgical removal. The rate at which degradation occurs should coincide as much as possible with the rate of tissue formation. Thus, while cells are fabricating their own natural structure around themselves, the matrix can provide structural integrity and eventually break down leaving the neotissue, newly formed tissue which can assume the mechanical load. Injectability is also preferred in some clinical applications. Suitable matrix materials are discussed in, for example, Ma and Elisseeff, ed. (2005) Scaffolding in Tissue Engineering, CRC, ISBN 1574445219; Saltzman (2004) Tissue Engineering: Engineering Principles for the Design of Replacement Organs and Tissues, Oxford ISBN 019514130X.

The biomaterial may be coated or impregnated with T-MPCs. Coating or impregnating may comprise contacting the T-MPCs with the biomaterial such that they are allowed to be adsorbed and/or absorbed onto and/or into the biomaterial. Coating may comprise adsorbing the T-MPCs onto the surface of the biomaterial. Coating or impregnation of the biomaterial may involve seeding T-MPCs onto or into the biomaterial. The biomaterial should allow the coated or impregnated T-MPCs cells to be released from the biomaterial when administered to or implanted in the subject. Biomaterial release kinetics may be altered by altering the structure, e.g. porosity, of the biomaterial.

The biomaterial can be supplemented with additional cells. For example, one can "seed" the biomaterial with feeder cells, which may be useful for supporting growth and maintenance of the T-MPCs. The subject to be treated may be any animal or human. In one embodiment, the subject is mammalian. In some embodiments, the subject is a human. In other embodiments, the subject is a non-human mammal. In certain embodiments, non-human mammals include rabbits, guinea pigs, rats, mice or other rodents (including any animal in the order Rodentia), cats, dogs, pigs, sheep, goats, cattle (including cows or any animal in the order Bos), horse (including any animal in the order Equidae), donkey, and non-human primates. The subject may be male or female. The subject may be a patient.

A matrix is used herein as an example of a biocompatible substance. However, the current invention is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable substance.

Kits

Also provided are kits. Such kits can include a therapeutic composition described herein and, in certain embodiments, instructions for administration. Instructions may be printed on paper or other substrate, or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit. Such kits can facilitate performance of the methods described herein. When supplied as a kit, the different components of the composition can be packaged in separate containers and admixed immediately before use. Components include, but are not limited to T-MPCs, culture media, and matrix or scaffold materials, as described herein. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include T-MPCs in a container with or without other components such as water, media, growth factors etc. Containers may include test tubes, vials, flasks, bottles, syringes, bags or pouch, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples describe embodiments of the present invention, and are not to be construed as limiting in any way the remainder of the disclosure.

Example 1: Detailed Protocol for the Generation of Human Tonsillar Stem Cells

Tonsils retrieved from tonsillectomy procedures have shown to be a good source of MPCs (Janjanin et al., (2008) Arthritis Res Ther 10:R83). However, tissues harvested from healthy donors would be preferable as a reliable source of stem cells. To this end a procedure was developed to generate highly proliferative multipotent stem cells from a small fragment of normal tonsillar tissue. Tonsils are lymphoid tissue anatomically located at the entrance of pharynx. Tonsillar tissues retrieved from tonsillectomy procedures were shown to be a good source of MPCs (Janjanin et al., (2008) Arthritis Res Ther 10:R83). However, for translational purposes, cells that can be retrieved from healthy donors without the risk of major complications and donor morbidity are preferred as a reliable source for stem cells. Here a novel procedure for the isolation of MPCs from a biopsy-sized sample of a human tonsil is reported. Tonsillar MPCs (T-MPCs) have been isolated from multiple donors across a spectrum of age, sex, and race and successfully expand in culture. They have been characterized by cell surface markers, in vitro expansion and differentiation potential. Overall, this study highlights tonsillar biopsy as an excellent source of MPCs and a viable alternative to currently used sources such as bone marrow and adipose tissue.

The enzymes and procedures used in the isolation and expansion of MPCs are different from those previously described. Previous protocols to generate T-MPCs are limited to tissue discarded following tonsillectomy. The currently developed procedure is so efficient there is no need for a full tonsillectomy and can be achieved with a small tonsillar biopsy from healthy a donor and minimizes the risk, pain and potential complications related to general anesthesia and surgical tonsillectomy. Using tonsillar tissue as a source of stem cells provides a robust yield with samples as small as 0.6 cc and avoids incisions to the body, risk of infection, and can be done in a fully awake patient in the office without the need for general anesthesia. Commonly, there are clinical indications when tonsillar tissue is sampled or biopsied in an outpatient environment with relatively little morbidity for diagnostic purposes. Obtaining a tonsillar sample takes minutes and requires adequate illumination, as well as topical and local anesthetics similar to that of a dental procedure. The tonsil area is first anesthetized with topical Cetacaine spray; next, a small amount (~1 cc) of lidocaine is injected into the area to be sampled to provide anesthesia and vasoconstriction. At this point, a biopsy forceps (or instrument designed to obtain tissue with minimal trauma) is used to obtain the tonsil sample and it is placed in a specimen cup and preserved on ice prior to processing and harvesting MPCs. For such small samples, there is a minimal risk, including self-limiting bleeding and local discomfort that can be managed with analgesics (Tylenol) for 2-3 days. This protocol offers new alternatives to the many patients who will benefit from cell therapy or need MPCs for repair due to surgical removal of tumors, trauma, congenital defects and other pathologies without the obligatory second surgical site and morbidity resulting from invasive procedures required for harvesting autologous tissue. This protocol provides an improved initial yield of MPCs as well as MPCs that have an ability to proliferate longer in tissue culture. An average of $3.5 \times 10^9$ MPCs were generated after one passage in vitro, from 0.6 cc tonsil tissue. T-MPCs cells derived from older donors (age 30 and up to 59) were able to be expanded up to 15 times, whereas T-MPCs cells derived from pediatric donors (age 3-7) can be expanded over 25 times.

MPCs have been shown to migrate to sites of tissue injury and have strong immunosuppressive properties that can be exploited for successful autologous and for allogenic transplantations. Furthermore, not only in disease treatment, hMPCs are also equally used in drug discovery applications as replacements for primary cells and animal models for initial toxicity and screening of new compounds. As of October of 2016, there are 652 clinical trials with MPCs, of which 43 are at phase 3 and 3 are at phase 4.

The clinical trials fall into the following broad categories: Blood and Lymph Conditions, Cancers and Other Neoplasms, Digestive System Diseases, Diseases and Abnormalities at or Before Birth, Ear Nose and Throat Diseases, Eye Diseases, Gland and Hormone Related Diseases, Heart and Blood Diseases, Immune System Diseases, Mouth and Tooth Diseases, Muscle, Bone, and Cartilage Diseases, Nervous System Diseases, Nutritional and Metabolic Diseases, Occupational Diseases, Respiratory Tract (Lung and Bronchial) Diseases, Skin and Connective Tissue Diseases, Substance Related Disorders, Symptoms and General Pathology, Urinary Tract, Sexual Organs, and Pregnancy Conditions, Viral Diseases, Wounds and Injuries.

More specifically, clinical trials involving MPCs target the following diseases and conditions: Ulcerative Colitis, Diabetes Mellitus, Type 1, Liver Cirrhosis, Nonunion Fractures, Diabetic Foot, Critical Limb Ischemia, Dilated Cardiomyopathy, Autoimmune Diseases; Immune System Diseases; Demyelinating Diseases; Nervous System Diseases; Demyelinating Autoimmune Diseases, CNS; Autoimmune Diseases of the Nervous System (MS), Sjogren's Syndrome, Graft Versus Host Disease; Chronic and Expanded Graft Versus Host Disease, Middle Cerebral Artery Infarction, Osteoarthritis, Aplastic Anemia, Maxillary Cyst; Bone Loss of Substance, Spinal Cord Injury, Parkinson's Disease, Crohn's Disease, Acute Myocardial Infarction, Multiple Sclerosis, Hematological Malignancies, Organ Transplantation, Ischemia; Stroke, Systemic Sclerosis, Hereditary Ataxia, Liver Failure, Retinitis Pigmentosa, Kidney Transplant; Rheumatoid Arthritis, Lumbar Spondylolisthesis Involving L4-L5, Chronic Allograft Nephropathy, Degenerative Arthritis; Chondral Defects; Osteochondral Defects, Progressive Multiple Sclerosis; Neuromyelitis Optica, Primary Biliary Cirrhosis, Osteonecrosis of the Femoral Head, Pened Chest Surgery for Programmes Coronary Bypass, Lupus Nephritis, Wilson's Disease, Multiple System Atrophy, Burns, Intervertebral Disc Disease, Chronic Myocardial Ischemia; Left Ventricular Dysfunction, Relapsing-Remitting Multiple Sclerosis; Secondary Progressive Multiple Sclerosis; Progressive Relapsing Multiple Sclerosis, Tibial Fracture, Bone Cyst, Buerger's Disease, Amyotrophic Lateral Sclerosis, Allogeneic Stem Cell Transplantation, Idiopathic Pulmonary Fibrosis, Type 2 Diabetes Mellitus, Refractory Systemic Lupus Erythematosus, Leukemia, Myeloid, Acute; Leukemia, Lymphoblastic, Acute; Leukemia, Myelocytic, Chronic; Myeloproliferative Disorders; Myelodysplastic Syndromes; Multiple Myeloma; Leukemia, Lymphocytic, Chronic; Hodgkin's Disease; Lymphoma, Non-Hodgkin, Degenerative Arthritis, Myelodysplastic Syndrome, ST-Elevation Myocardial Infarction, Pulmonary Disease, Chronic Obstructive; Pulmonary Emphysema; Chronic Bronchitis, Lower Back Pain; Disc Degeneration, Articular Cartilage Lesion of the Femoral Condyle, Osteoporotic Fractures, Bone Neoplasms, Solid Tumors; Acute Kidney Injury, Hereditary Cerebellar Ataxia, Primary Disease, Autism, Limbus Corneae Insufficiency Syndrome, Wound Healing, Dementia of the Alzheimer's Type, Non-ischemic Dilated Cardiomyopathy, Stroke, Epidermolysis Bullosa, Tibia or Femur Pseudo-arthrosis, Recovery Following Partial Medial Meniscectomy, Human Immunodeficiency Virus, Stable Angina; Heart Failure; Atherosclerosis; Multivessel Coronary Artery Disease, Osteogenesis Imperfecta, Emphysema, Progressive Hemifacial Atrophy; Romberg's Disease, Complex Perianal Fistula, Multiple Trauma, Osteodysplasia, Tibiotalar Arthrodesis; Subtalar Arthrodesis; Calcaneocuboid Arthrodesis; Talonavicular Arthrodesis; Double Arthrodesis (i.e. Calcaneocuboid and Talonavicular); Triple Arthrodesis (i.e. Subtalar, Calcaneocuboid, and Talonavicular), Recto-vaginal Fistula, Peripheral Vascular Diseases, Prostate Cancer; Erectile Dysfunction, Diabetic Wounds; Venous Stasis Wounds, Ovarian Cancer; Sarcoma; Small Intestine Cancer.

The methods of generating MPCs from tonsillar tissue are now described.

The following protocol can be used for any solid (non-boney) tissue. It yields 0.2-1 billion viable cells per 1 gram of tissue. Different tissues yield different amount of multipotent stem cells and their potency varies. The more vascularized the tissue is, the higher the fraction of stem cells.

Additionally, using this protocol with tonsillar tissue initially yields other mononuclear cells such as T-lymphocytes and B-lymphocytes which are unique to the tonsillar tissue. These cells may be useful for other applications (B-lymphocytes for production of immunoglobulins and extrathymic T-cells for example). Some of these cells can attach to the plate initially. However, without specific purification or specific mitogenic activation, the media conditions do not support the growth of these cells, and they disappear after the first cell passage to give high purity of T-MPCs.

Volumes and vessels described here are per 1 gram of tissue, but can be adjusted accordingly for larger amounts of tissue.

IMDM containing 1.6 U/ml Liberase enzyme, 100 μg/ml deoxyribonuclease was prepared in an appropriate volume. Throughout the protocol it was ensured that the tubes and vessels containing cells were not deprived of oxygen. Further, tubes were not filled more than 50% to maintain high cell viability.

Tonsillar tissue was maintained on ice in a sterile environment. Tissue was treated with sterile equipment, consumables and solutions in a biological hood.

Upon receipt of a tonsillar tissue specimen, any corresponding data is documented, including, but not limited to, a material receipt note (MRN), date of birth (DOB), age at the time of tissue harvesting, indication for surgery, race, sex of the subject, and weight of specimen.

The tissue was washed twice with DPBS in 50 ml tube until no blood is visible and solution is clear.

The tissue was washed twice with IMDM.

Larger tissue is minced into very small 1 mm fragments in 10 ml IMDM in a 6 cm sterile dish. Best results are achieved with blunt scissors or blade. If necessary, the medium and fragments are transferred to a 50 ml tube to finish mincing. Fragments should fit through 10 ml pipette.

Minced tissue is washed in DPBS twice or until no more blood is visible. The supernatant is collected and transferred to a 50 ml tube to salvage cells and spin with the other tubes. The washing is repeated until the supernatant is clear. If necessary, any remaining large fragments are further minced and washed. All washes are done by spinning at 500 rpm for 5 minutes, supernatant is removed, tubes is tapped to release the pellet and 5 ml of IMDM or DPBS is used per wash.

The supernatant is removed and 10 ml of IMDM containing 1.6 U/ml Liberase enzyme, 100 μg/ml deoxyribonuclease is added to the fragmented tissue sample. The sample is incubated for 45 minutes to 90 minutes at 37° C. (the tubes are not closed all the way to allow some air in). The tubes are shaken every 15 minutes to mix the cells.

Digestion is complete when cell fragments become loose.

The medium and fragments are transferred to a plate and passed multiple times, with pressure, through a 10 ml pipette to release the cells.

Any leftover fragments are mechanically mashed thoroughly until no fragments are left. This can be done by using the rough side of frosted slides against each other or using an equivalent technique. If there are fragments that do not break easily, the fragments and medium IMDM containing 1.6 U/ml Liberase enzyme and 100 μg/ml deoxyribonuclease may be returned to the tube for longer incubation. Upon completion of the digestion, no fragments are left and the medium becomes opaque as it is loaded with cells.

Cells are collected into 15 ml tubes, spun at 500 rpm for 5 minutes, and washed in DPBS to remove any dead cells and red blood cells. The supernatant is transferred to a different tube to salvage additional cells. The pelleted cells are gently released from the tube by tapping and washed again. At this point a pellet of red blood cells (RBC) is be formed below the whiter pellet containing the stem cells. To purify the pellet containing the stem cells, the supernatant is carefully removed and a micropipette is used to transfer the upper (white part) of the pelleted cells into a fresh tube. This step is repeated until no red blood cells are visible in the pellet.

The pellet is re-suspended in fresh T-MPC medium and passed through a cell strainer 70 um nylon mesh to remove cell clumps and debris. T-MPCs medium contains DMEM, 10% heat inactivated FBS, 1× GlutaMAX, 1% sodium pyruvate, 1% non-essential amino acids, 1% penicillin/streptomycin and 100 μM of beta-mercaptoethanol.

The cells are centrifuged at 500 rpm for 5 minutes and the media is removed. The cells are then supplemented with fresh T-MPC medium.

Cell viability is determined (e.g., using trypan blue or other cell viability assessment methods).

Cells are cultured in fresh T-MPC medium at a density equivalent to $5 \times 10^6$ cells per 10 cm plate. Cells are split by using accutase when in under-confluent conditions (e.g., 70-80% confluence) to avoid spontaneous differentiation.

For cryogenic storage, cells are pelleted and the cell pellet is resuspended in freezing medium (10% DMSO in FBS). The cells are then stored at −80° C. for one day. For long-term storage (more than a few months) the frozen cells are transferred to liquid nitrogen.

One advantage of this protocol is that no clonal isolation is necessary. By P1 99.9% of the cells are CD44, CD90 positive. Therefore, this protocol avoids unnecessary in vitro aging during cell expansion.

Xenofree Cell Expansion Protocol

For xenofree cell expansion, culture dishes are coated with 20 μg/ml fibronectin in PBS containing $Ca^{2+}$ and $Mg^{2+}$.

For cryopreservation, cells are harvested by accutase, fresh medium (Xenofree medium as detailed in Table 1) is added and single cell suspension is made. Cells are centrifuged at 500 rpm for 5 minutes. Supernatant is removed and 1 ml of cold (4° C.) xenofree freezing medium (e.g., 10% DMSO in University of Wisconsin solution (also called Viaspan) or 10% DMSO in HypoThermosol (HTS)) is added to the cells and cells are transferred to a freezing vial and taken to −80° C. at least one day. For long term storage (more than a few months) transfer to liquid nitrogen.

TABLE 1

| Xenofree medium | | |
| --- | --- | --- |
| Reagent | Stock | End conc. |
| IMDM (4 mM glutamate, HEPES) | | X1 |
| Insulin | X100 10 mg/ml | 100 µg/ml |
| Holo human transferin | X2000 10 mg/ml | 5 µg/ml |
| Sodium pyruvate | X100 100 mM | 1 mM |
| GlutaMax ( 200 mM L-alanyl-L-glutamine dipeptide in 0.85% NaCl.) | X100 200 mM | 2 mM |
| NEAA | X100 | 1% |
| Human serum albumin or BSA fraction V | | 1 gr/100 ml |

Example 2: Multipotent Progenitor Cells from Human Tonsils

Human adult multipotent progenitor cells (MPCs) hold the potential for the treatment of numerous conditions and degenerative diseases. MPCs possess major advantages over both embryonic stem (ES) cells and induced pluripotent stem (iPS), as they can be derived from donors at any age, and therefore pose no ethical concerns or risk of teratoma tumor formation in vivo. Furthermore, they have a natural ability to differentiate and secrete factors that promote tissue healing without genetic manipulation. However, at present, clinical applications of MPCs are limited by a shortage of a reliable, standardized and easily assessable tissue source, which does not rely on specimen discarded from unrelated surgical procedures.

Here it is demonstrated that highly proliferative tonsillar MPCs (T-MPCs) can be harvested from a very small fragment of tonsillar tissue. This procedure provides a robust yield of tonsillar MPCs, which can be obtained in a non-surgical setting. Millions of stem cells can be harvested from a sample smaller than 1 gram, which can be collected from a fully awake donor in an outpatient setting without the need for general anesthesia or hospitalization. This study identifies tonsillar biopsy as an abundant source of adult stem cells for regenerative medicine. This protocol allows extraction of stem cells from a very small fragment of tissue (0.6 cc) by a minimally invasive procedure. Using this technique, 14 MPC lines were established, with high yield. Further, the experiments presented herein demonstrate that T-MPCs are isolated, propagated, and maintained as well as differentiated into multiple tissues such as bone, cartilage, neurons and fat. These protocols demonstrate greater efficiency of isolation of MPCs from adult tissues compared to other procedures and enables massive in vitro expansion of MPCs required for regenerative medicine.

The Methods used in the Experiments are now described.

Isolation and Expansion of Stem Cells from Human Tonsils

A tonsillar biopsy was taken at the time of tonsillectomy and the tissue was then processed as demonstrated in FIG. 1. Fresh tonsil tissue specimens were obtained from the University of Maryland Medical Center, with an average weight of 0.88±0.1 (Average ±S.E.M) grams tissue per specimen. Tonsil specimens were kept in sterile conditions and the procedure was done under a biological hood. The tissue was washed twice with DPBS (Life Technologies) followed by washing with IMDM medium (Hyclone). The tissue was then fragmented in a 6 cm sterile culture plate into very small pieces in IMDM medium. Minced tissue was collected into a 50 ml tube, centrifuged at 500 rpm for 1 minute and washed repeatedly with DPBS until no more blood was visible. Tissue was then incubated for the duration of 45 minutes at 37° C. in 10 ml IMDM containing 1.6 U/ml Liberase (Roche) and 100 µg/ml deoxyribonuclease (Sigma) with additional time added as needed to achieve complete digestion. At all stages of this protocol, the tube cap was not tightened to allow air into the tube and to prevent hypoxic conditions. To maximize yield, tubes were agitated every 15 minutes. Remaining tissue fragments were subjected to further disruption by application of mechanical force between the rough label sides of two frosted microscope slides, followed by passage through a pipette to allow release of single cells. This step was repeated until no tissue fragments were visible. Cells were collected into 15 ml tubes and washed with 5 ml DPBS, followed by centrifugation at 500 rpm for 5 minutes. The cell pellet was transferred to a fresh tube until a clean pellet was achieved. Cells were suspended in fresh T-MPC medium (500 ml DMEM (Life Technologies), 10% heat inactivated FBS (Sigma), 1× GlutaMAX (Invitrogen), 1% sodium pyruvate (Invitrogen), 1% non-essential amino acids (Invitrogen), 1% penicillin/streptomycin (Life Technologies), and 100 µM of beta-mercaptoethanol (Life Technologies)). Cells were then passed through 70 µm nylon mesh filter. Cells were stained with trypan blue to determine cell viability. Five million cells were seeded per 10 cm plates (total 10 plates) per donor. Remaining cells were aliquoted to 5 million cells per vial and were taken for cryogenic preservation. The next day, cells were washed thoroughly to remove non-adherent cells and medium was replaced with fresh T-MPC medium. Visible individual colonies were typically formed within 1 week. Clones were dissociated by Accutase, isolated, and seeded separately in one well of a six-well plate to make passage 1 (P1). To keep the culture potential and to avoid loss of clones due to aging, clones were randomly taken per patient for further analysis, and the remainder of the clones frozen at P1. Clones were then continuously maintained by subculturing at low densities of $10^5$ cells per 10-cm plate and harvested at 70% confluency thereafter.

Population Doubling Assay

The cells attached after tissue harvesting were considered passage zero (P0) with passage number corresponding to the number of times the cells were sub-cultured. For each culture passage, $2.5 \times 10^4$ of T-MPCs per well were seeded in six well plates in triplicates. Cells were harvested by accutase (Millipore) every five days to ensure cells are constantly grown in sub-confluence conditions. Upon harvesting by accutase, cells were counted and $2.5 \times 10^4$ cells were re-seeded in 6 well plates in triplicates. Cells were continuously sub-cultured until the cells stopped replicating and culture reached cellular senescence. The cumulative population doublings (PD) is the total number of times the cell population have doubled during subculture and calculated by continuously adding the PD per each passage. The number of population doublings (PD) per donor was calculated using the formula:

$$PD = \text{Ln}\left(\frac{Nt}{N0}\right) * 3.33,$$

where N0 is the number of cells at seeding and Nt is the number of cells counted at harvesting.

Population Doubling Assay and Doubling Time in Xeno-Free Medium

To culture T-MPCs in xeno-free, serum free conditions, culture plates were first pre-coated with 20 µg/ml fibronectin in PBS. T-MPCs were seeded and passaged once in every 7 days in fibronectin (Thermo) coated 12-well plates at approximately 10% confluence (3500 cells per well). Cells were Growth rate was calculated as above. The doubling time (Td) was calculated as the log 2 of the duration of culture (hours), divided by the log(Final cell number) minus log(Number of cell seeded):

$$Td = \frac{\log(2)}{\log(1+r)} \times \frac{24\text{ h}}{\text{time(hours)}}$$

Flow Cytometry Analysis

T-MPCs were harvested using accutase from 70%-confluent plates. Cells were fixed in 4% paraformaldehyde for 10 minutes and samples were taken for immunofluorescence staining and incubated with corresponding antibodies: CD44-Alexa488, CD90 Alexa647, CD45 Alexa647, CD31-Alexa594 (Bioloegend; 1:100 dilution) in blocking solution (10% FBS, 1% BSA in DPBS) on ice for 30 minutes. The negative control cells were also incubated in blocking solution without primary antibody. After three washes with blocking solution, cells were mixed with the corresponding secondary antibody in blocking solution and incubated for 20 minutes on ice. Cells were washed with DPBS and analyzed by flow cytometry.

Flow Cytometry for Pluripotent Stem Cells Markers

T-MPCs were harvested and fixed as described above and incubated with corresponding antibodies: SSEA4 (1:100), TRA-1-81 (1:250), and TRA-1-60 (1:250) (Cell Signaling) in blocking solution (10% FBS, 1% BSA in DPBS) on ice for 30 minutes. Mouse embryonic stem cells were used as positive controls. Negative control MPCs were incubated with mouse IgG or rat IgG with the corresponding secondary antibodies. Following washes with blocking solution, cells were mixed with the corresponding secondary antibody in blocking solution and incubated for 20 minutes on ice. Cells were washed with DPBS and analyzed by flow cytometer.

Osteogenic Differentiation Assay

To induce differentiation toward the bone lineage, osteogenic supplement stock solution was prepared using 1.5 mM L-ascorbic acid 2-phosphate (Sigma), 100 mM β-glycerophosphate (Sigma), 100 nM dexamethasone (Sigma) in 5 ml of warm penicillin (10,000 units/ml) and streptomycin (10,000 mg/ml) (Life Technologies). The resulting mixture was mixed with 45 ml Fetal Bovine Serum (FBS) to prepare 50 ml of 10× osteogenic supplements stock solution. Fresh medium was prepared by diluting osteogenic supplements to phenol red free DMEM (Life Technologies). Twenty thousand ($2\times10^4$) T-MPC cells were seeded on 24 well plates. Next day, cells were washed with DPBS, followed by addition of complete regular medium or osteogenic medium to the corresponding wells. The medium was changed every 4 days and cells were differentiated for 21 days.

Alizarin Red S Staining

To validate osteogenic differentiation, calcium deposits can be demonstrated by Alizarin Red S staining. Twenty thousand cells ($2\times10^4$) were seeded on 24 well plates. A day after seeding, cells were washed with DPBS and then allowed to grow in either complete or osteoblast differentiation medium for 28 days. Calcium deposits are an indication of successful differentiation of MPC into osteoblasts. Cells differentiated in osteogenic conditions and undifferentiated controls cells were fixed by incubating with 4% paraformaldehyde at room temperature for 30 minutes. Cells were stained with 2% Alizarin Red S solution (AMRESCO) in double distilled water (pH 4.4-4.3) at room temperature in the dark for 45 minutes, washed with double distilled water. Samples were photographed to visualize bright orange-red color in calcified osteoblasts.

Chondrogenic Differentiation Assay

To induce cartilage differentiation of T-MPCs, cells suspension ($10^7$ cells per ml) was prepared. Cells were seeded as droplets of 2 µl of cell suspension in dry 3.5 cm plates. Cell droplets were incubated for 1-2 hours in 5% CO2 at 37° C. After 1 hour, cells were observed to confirm adherence to the plate. Then, 2 ml chondrogenesis differentiation medium (StemPro, chondrogenesis differentiation kit, Life technologies) was added slowly and gently to the plate without disturbing the cells. Colonies presented proteoglycans within about 7-21 days to two weeks after seeding.

Alcian Blue 8GX Staining

To demonstrate proteoglycan synthesis by chondrocytes and cartilage differentiation, differentiated cells treated with chondrogenic medium and undifferentiated control cells were fixed by incubating with 4% paraformaldehyde at room temperature for 10 minutes. The cells were washed twice with PBS, gently rinsed with ddH$_2$O, and stained with Alcian blue 8GX solution (Fluka analytical) for 30 minutes at room temperature. Then stained cells were washed with running tap water for 2 minutes, rinsed with distilled water, and staining was documented using a phase contrast microscope to demonstrate proteoglycans in blue.

Adipogenic Differentiation Assay

To differentiate T-MPCs into adipocytes, adipogenic medium was made using phenol red free DMEM, supplemented with 10% Fetal Bovine Serum, 3-isobutyl-1-methylxanthine (0.5 mM), Dexamethasone (10 µM), Insulin (10 µg/ml) (Sigma), 1% penicillin/streptomycin (Life Technologies). Twenty thousand ($2\times10^4$) T-MPCs were seeded on 24 well plates. The next day, attached T-MPCs were washed with PBS and 1 ml of freshly prepared adipogenic medium was added to each well. Medium was changed every 4 days. Cells were allowed to grow in adipogenic medium for 3 weeks.

Oil Red O Staining

Differentiated adipocytes consist predominantly of lipid droplets which can be visualized by Oil Red O staining. Cells differentiated in adipogenic medium and undifferentiated control cells were fixed with 4% PFA for 10 minutes at room temp, washed twice with PBS, and incubated with 2 ml 60% isopropanol at room temp for 5 minutes. Isopropanol solution was discarded and 2 ml working solution of Oil Red O (Sigma) was added to each well and cells were incubated for 5 minutes at room temperature. The cells were rinsed with tap water until all residual stain was removed and the water was clear. Lipids droplets appear red and stained cells were demonstrated using a phase contrast microscope.

Total RNA Extraction and Generation of cDNA

Total RNA was extracted from $10^6$ differentiated or undifferentiated control cells using Qiagen RNeasy mini Kit, following the manufacturer protocol. Per each sample, RT-PCR was done by using 1 µg of total RNA to reverse transcribe in cDNA by Superscript III (Invitrogen) following the manufacturer's instructions.

Real Time qPCR Analyses for Differentiation Markers

To define upregulation in differentiation related genes by real-time qPCR, 10 ng cDNA of each sample was used per reaction in triplicates, using SYBR green I Master solution (Roche) following the manufacturer's protocol. LightCycler 480 II machine (Roche) was used for qPCR analysis. Fold induction was calculated by delta-delta Ct method using 200 ng of each primer to determine the target gene expression. Primers used in this study are listed in Table 2: Osteoblast markers: BMP2, OPN, OCN, ALP, RUNX2. Osteocyte markers: FGF23, DMP1, MEPE, SOST. Control marker: RPLP0. Adipogenic markers: ACAN, Leptin. Chondrogenic markers: ATP2A2, COL10A1, PPRAG.

TABLE 2

A list of osteoblast, adipocyte and chondrocyte primers.

| Primer | Fwd (5'-3') | SEQ ID NO: | Rev (5'-3') | SEQ ID NO: |
|---|---|---|---|---|
| BMP2 | CCCTACATGCTAGACCTGTATC | 1 | GTTGTTTTCCCACTCGTTTCTG | 2 |
| OPN | CCTTCCAAGTAAGTCCAACGAA | 3 | GACAACTGGAGTGAAAACTTCG | 4 |
| OCN | ATGAGAGCCCTCACACTCCTC | 5 | GCCGTAGAAGCGCCGATAGGC | 6 |
| ALP | TGGAGCTTCAGAAGCTCAACACCA | 7 | ATCTCGTTGTCTGAGTACCAGTCC | 8 |
| RUNX2 | TTTAGGGCGCATTCCTCATC | 9 | GGAGGGCCGTGGGTTCT | 10 |
| FGF23 | TTGGATCACACTATTTCGACCC | 11 | GAAGTGAATTAGGGGGATCTCG | 12 |
| DMP1 | TCTTTGTGAACTACGGAGGGTA | 13 | TGAGCCAAATGACCCTTCCA | 14 |
| MEPE | GAGGAAAAGGTAGACTGAGATTCT | 15 | GGGACAAATCTTTCTTTCTTTCCT | 16 |
| SOST | CAAGAATGATGCCACGGAAATC | 17 | GGACACGTCTTTGGTCTCAA | 18 |
| RPLP0 | CAGCAAGTGGGAAGGTGTAATCC | 19 | CCCATTCTATCATCAACGGGTACAA | 20 |
| ACAN | TGATGTTCCCTGCAATTACCAC | 21 | CAAAAAGCGACAAGAAGAGGAC | 22 |
| Leptin | ATTTTCAGAAGAGAACGGACATTC | 23 | TGCTCCCCTTCTTCAAAATGTA | 24 |
| ATP2A2 | AACTACCTGGAACCTGCAATAC | 25 | GGGTTGGTAGATGTGTTGCTAA | 26 |
| COL10A1 | GAGTAAAGGTATAGCAGTAAGAGGA | 27 | CATATGGTCCTCTCTCTCCTGG | 28 |
| PPRAG | AAGACAACAGACAAATCAACCG | 29 | GTCTTCTTGATCACCTGCAGTA | 30 |

Fwd = forward primer, Rev = reverse primer.

Statistical Analysis

Student's t-Tests were performed to assess a significant difference in the fold change between differentiated cells and undifferentiated T-MPCs for each of the markers. These analyses were performed using Graph pad Prism. Results were considered to be statistically significant when $p \leq 0.05$. The software STATSTICA 13 and GraphPad Prism 5 were used for data analyses and formation of the figures.

The results of the experiments are now described.

Derivation of Adult Multipotent Stem Cells from a Small Amount of Tissue

The ideal source for an autologous graft, or for the generation of universal donors, is a tissue specimen that can be retrieved without the risk of major complications and donor morbidity. To this end, a procedure was developed to generate highly proliferative multipotent stem cells from a small sample of tonsillar tissue. This procedure successfully generated T-MPC cell lines from 14 donors (9 females and 5 males). These samples were distributed across three age groups: pediatric (age 3-12; n=7), young adults (age 20-35; n=5) and middle-aged (age 40-up; n=2) donors. To ensure tissue handling and achieve optimal results, tonsil tissue samples were put in a sterile vessel on wet ice and transferred to the laboratory within hours from tissue harvesting. However, even when samples were stored at 4° C. for up to 24 hours, no significant change in yield was observed. Upon arrival of the sample to the laboratory, its weight was recorded. The tissue then was minced in IMDM medium, enzymatically digested and any left fragments are mechanically dissociated until single cells are released to the medium. Cells are cultured to establish T-MPC lines (FIG. 1). T-MPCs were generated from samples that averaged 0.88±0.1 gram (mean±S.E.M.) with a high yield and efficiency. To test MPC isolation efficiency compared to traditional methods using collagenase type I (Lee et al., (2016) Cell Physiol Biochem, 38:83-93; Janjanin et al., (2008) Arthritis Res Ther 10:R83; Cho et al., (2012) Cytokine, 59:211-214) digestion for 30 minutes, fresh tonsillar tissues from three donors were used and compared for cell viability and yield. The results indicate that digestion with collagenase I in combination with Deoxyribonuclease leads to a partial digestion and poor cell viability <50% following a 30-minute digestion. Conversely, using Liberase and deoxyribonuclease I incubation for >45 minutes leads to an average cell viability of >90%. The number of cells isolated per 1 gram of tissue ranged from 0.2-1 billion cells with an average of $4.6 \times 10^8 \pm 5.4 \times 10^6$ (mean±S.E.M.) cells/gram. Next, samples of 5 million cells per 10 cm plates were seeded followed by overnight incubation in 37° C. in a 5% humidified incubator. Attached cells were allowed to grow and fill in the plate to establish P0 (Passage zero). Cells are harvested when plate reached 70% confluence which ranges 5 to 13 days in culture. This procedure yields an average of two million ($2 \times 10^6$) T-MPCs per plate. Therefore, within a week and prior to the first cell split, 1 gram of tonsil tissue yields an average of 6.2×10$^7$±4.4×10$^6$ (mean±S.E.M.) T-MPCs. These T-MPCs can then be further massively expanded in culture.

T-MPCs Express Mesenchymal Progenitor Cell Markers

Figures 2A, 2B, 2C, 2D:
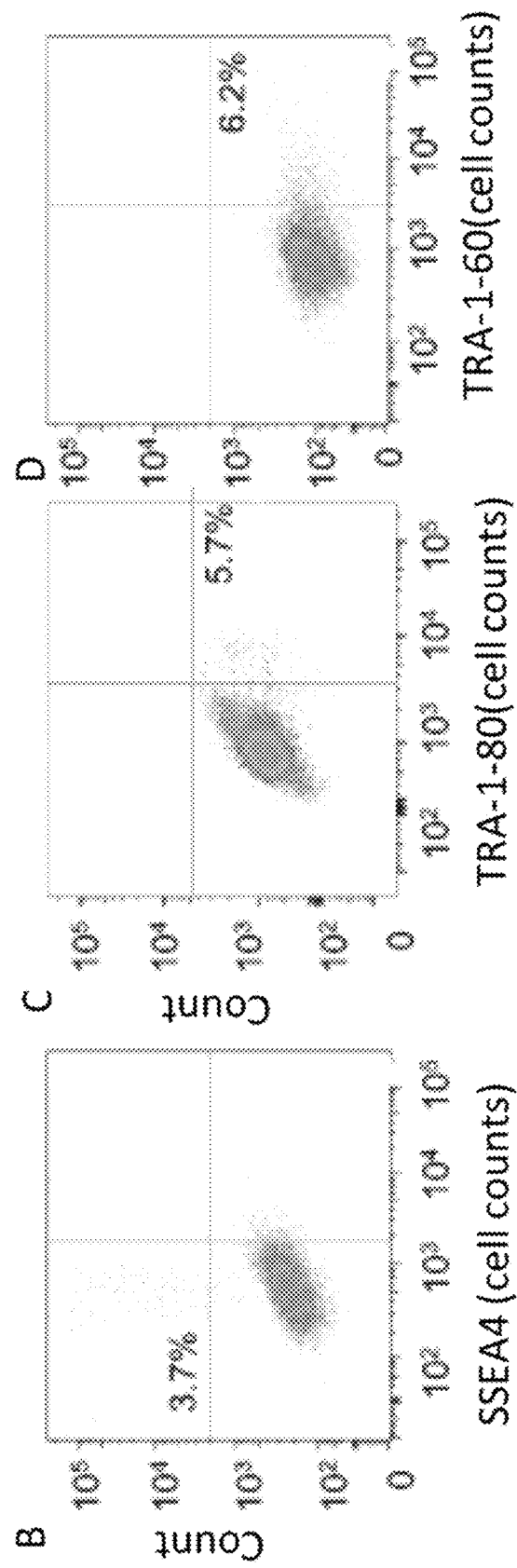
FIG. 2A through FIG. 2D, depicts exemplary experimental results demonstrating characterization of T-MPCs by immunostaining and flow cytometry.

Flow cytometry analysis MPC markers in T-MPCs from all 14 donors show that the T-MPCs are CD44 99.9%±0.03 positive, CD90 95.12%±0.52 (average S.E.M.), while cells were negative to CD45 and CD31 (n=7 donors) (FIG. 2). These results show tonsillar biopsy provides a high yield and purity of multipotent stem cells. Interestingly, a sub-population of T-MPCs expressing the pluripotency related surface markers SSEA-4 (3.7%), TRA-1-80 (5.7%) and TRA-1-60 (6.2%) was detected. These data demonstrate that there is a possibility to isolate and propagate a stem cell population of higher potency from this tissue.

T-MPCs are Highly Proliferative

Figures 3A, 3B, 3C, 3D:
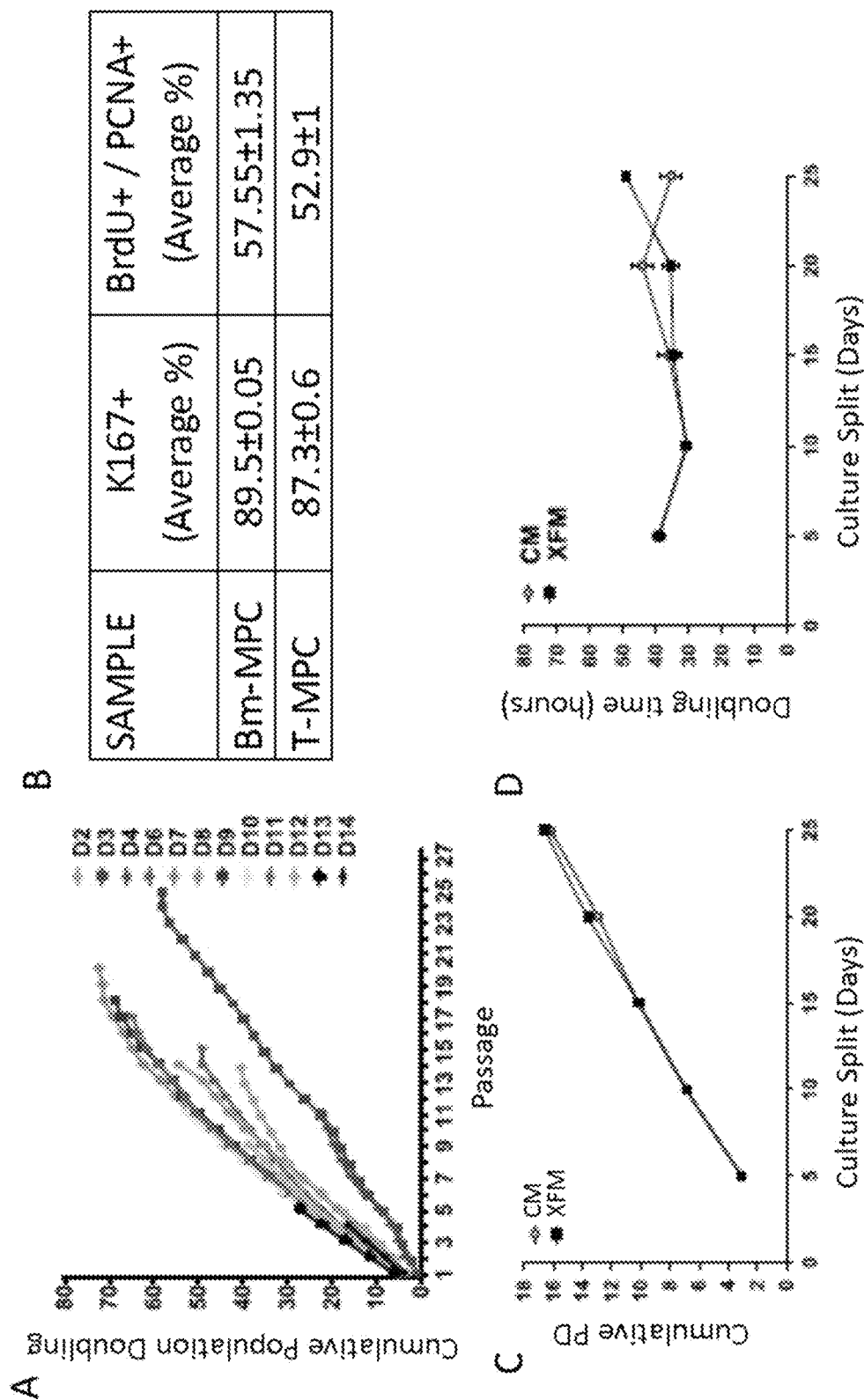
FIG. 3A through FIG. 3D, depicts exemplary experimental results demonstrating growth curves for T-MPC lines. Cells were split, counted, and $10^5$ tonsillar mesenchymal progenitor cells (T-MPCs) were plated per passage.

To determine the in vitro expansion efficiency per donor, population-doubling assays were performed. 2.5×10$^4$ T-MPCs were seeded per well in triplicates in 6 well plates and cells were split every 5 days to determine population doublings. A robust and highly proliferative population of cells was shown from all donors. The majority of the T-MPC lines presented constant proliferation rates for at least 15 passages with some extending beyond 19 passages. Cumulative population doubling (PD) ranged from 40 to 69 PDs (FIG. 3a). To find out whether the T-MPCs present active telomerase, telomerase activity was measured by TRAP assay using a TRAPEZE Telomerase Detection Kit. Consistent with the observation of finite population doublings of at least 40 population doublings, the results indicate that the T-MPCs are telomerase negative. Next, T-MPCs were analyzed by flow cytometry using the proliferation marker KI67 in cells from all 14 donors. The results show that 87.3±0.6% (mean±SEM) of the cells actively proliferate. To study the fraction of the cells in S phase, the cells were incubated with BrdU and flow cytometry was performed using anti-BrdU in combination with the S phase marker PCNA (FIG. 3b; Table 3 through Table 5). The data show T-MPC proliferation is comparable to BM-derived MPCs (FIG. 3b; Table 3 through Table 5).

TABLE 3

Expression of markers in Bm-MPCs and T-MPCs from 14 donors

| SAMPLE | CD90+/CD44+ (Average %) | SEM | CD105+/CD73+ (Average %) | SEM | CD19− (Average %) | SEM |
|---|---|---|---|---|---|---|
| Bm-MPC | 99.4 | 0.15 | 97.8 | 0.58 | 98.0 | 0.58 |
| Donor 1 | 99.6 | 0.19 | 97.4 | 1.18 | 98.3 | 1.18 |
| Donor 2 | 99.5 | 0.06 | 97.3 | 1.94 | 95.2 | 1.94 |
| Donor 3 | 97.8 | 0.12 | 98.3 | 0.36 | 97.0 | 0.36 |
| Donor 4 | 99.4 | 0.19 | 97.4 | 0.45 | 97.0 | 0.45 |
| Donor 5 | 99.6 | 0.12 | 96.8 | 0.37 | 97.0 | 0.37 |
| Donor 6 | 99.5 | 0.24 | 99.7 | 0.25 | 99.6 | 0.25 |
| Donor 7 | 98.2 | 1.13 | 96.8 | 0.41 | 96.5 | 0.41 |
| Donor 8 | 96.6 | 0.89 | 99.2 | 0.64 | 98.8 | 0.64 |
| Donor 9 | 99.4 | 0.14 | 96.4 | 0.20 | 97.9 | 0.20 |
| Donor 10 | 99.1 | 0.12 | 96.9 | 0.21 | 98.2 | 0.21 |
| Donor 11 | 99.2 | 0.15 | 97.0 | 0.44 | 97.8 | 0.44 |
| Donor 12 | 98.6 | 0.12 | 96.6 | 0.33 | 97.6 | 0.33 |
| Donor 13 | 98.2 | 0.58 | 97.7 | 0.64 | 96.8 | 0.64 |
| Donor 14 | 95.1 | 0.33 | 98.0 | 0.82 | 97.5 | 0.68 |
| Average | 98.6 | | 97.5 | | 97.5 | |
| SEM | 0.3 | | 0.3 | | 0.3 | |

TABLE 4

Expression of markers in Bm-MPCs and T-MPCs from 14 donors

| SAMPLE | HLA-DR− (Average %) | SEM | KI67+ (Average %) | SEM | BrdU+/PCNA+ (Average %) | SEM |
|---|---|---|---|---|---|---|
| Bm-MPC | 98.9 | 0.62 | 89.5 | 0.05 | 57.6 | 1.35 |
| Donor 1 | 99.6 | 0.06 | 87.5 | 1.53 | 50.4 | 1.15 |
| Donor 2 | 99.5 | 0.09 | 88.2 | 2.27 | 43.1 | 0.85 |
| Donor 3 | 100 | 0.03 | 89.6 | 0.57 | 52.2 | 0.45 |
| Donor 4 | 99.9 | 0.00 | 85.9 | 0.51 | 50.1 | 2.55 |
| Donor 5 | 99.9 | 0.03 | 87.9 | 1.00 | 54.9 | 1.20 |
| Donor 6 | 99.3 | 0.53 | 87.1 | 0.25 | 57.3 | 0.80 |
| Donor 7 | 96.6 | 1.64 | 86.2 | 0.69 | 55.7 | 0.35 |
| Donor 8 | 98.8 | 0.90 | 81.0 | 0.84 | 50.3 | 1.05 |
| Donor 9 | 99.9 | 0.08 | 89.5 | 0.45 | 51.3 | 2.05 |
| Donor 10 | 99.9 | 0.07 | 85.0 | 1.08 | 51.7 | 2.00 |
| Donor 11 | 99.9 | 0.03 | 87.0 | 0.40 | 52.5 | 0.40 |
| Donor 12 | 99.9 | 0.03 | 87.7 | 4.27 | 56.3 | 0.80 |
| Donor 13 | 99.0 | 0.29 | 86.7 | 1.30 | 54.2 | 2.00 |
| Donor 14 | 99.0 | 0.10 | 91.3 | 1.00 | 56.9 | 0.10 |
| Average | 99.3 | | 87.3 | | 52.9 | |
| SEM | 0.2 | | 0.6 | | 1.0 | |

TABLE 5

Differentiation of Bm-MPCs and T-MPCs from 14 donors

| SAMPLE | Osteogenic differentiataion | Chondrogenic differentiataion | Adipogenic differentiataion |
|---|---|---|---|
| Bm-MPC | High | High | Moderate |
| Donor 1 | High | High | High |
| Donor 2 | High | High | High |
| Donor 3 | High | High | Moderate |
| Donor 4 | High | High | High |
| Donor 5 | High | High | High |
| Donor 6 | High | High | High |
| Donor 7 | High | High | ND |
| Donor 8 | High | High | High |
| Donor 9 | High | ND | High |
| Donor 10 | High | High | High |
| Donor 11 | High | High | High |
| Donor 12 | High | High | High |
| Donor 13 | High | ND | High |
| Donor 14 | High | ND | High |

Expansion of T-MPCs in Xeno-Free Medium

Next, the expansion potential of T-MPCs in xeno-free medium was evaluated. In order to avoid risks of viral cross contamination and to increase reproducibility of expansion procedures, cells were required to efficiently grow in the absence of animal-derived products and in defined medium. Therefore, the ability of the cells to expand in xenofree medium with defined soluble factors was evaluated. The results show that the isolated T-MPCs can efficiently grow for at least 20 days in predefined culture conditions to achieve 18 population doublings. This represents a fold increase of 2.6×10$^5$ and demonstrates the massive cell expansion capacity of T-MPCs in xeno-free medium (FIG. 3c and FIG. 3d).

Osteogenic Differentiation of T-MPCs

Figures 4A, 4B, 4C, 4D, 4E, 4F, 4G, 4H, 4I, 4J:
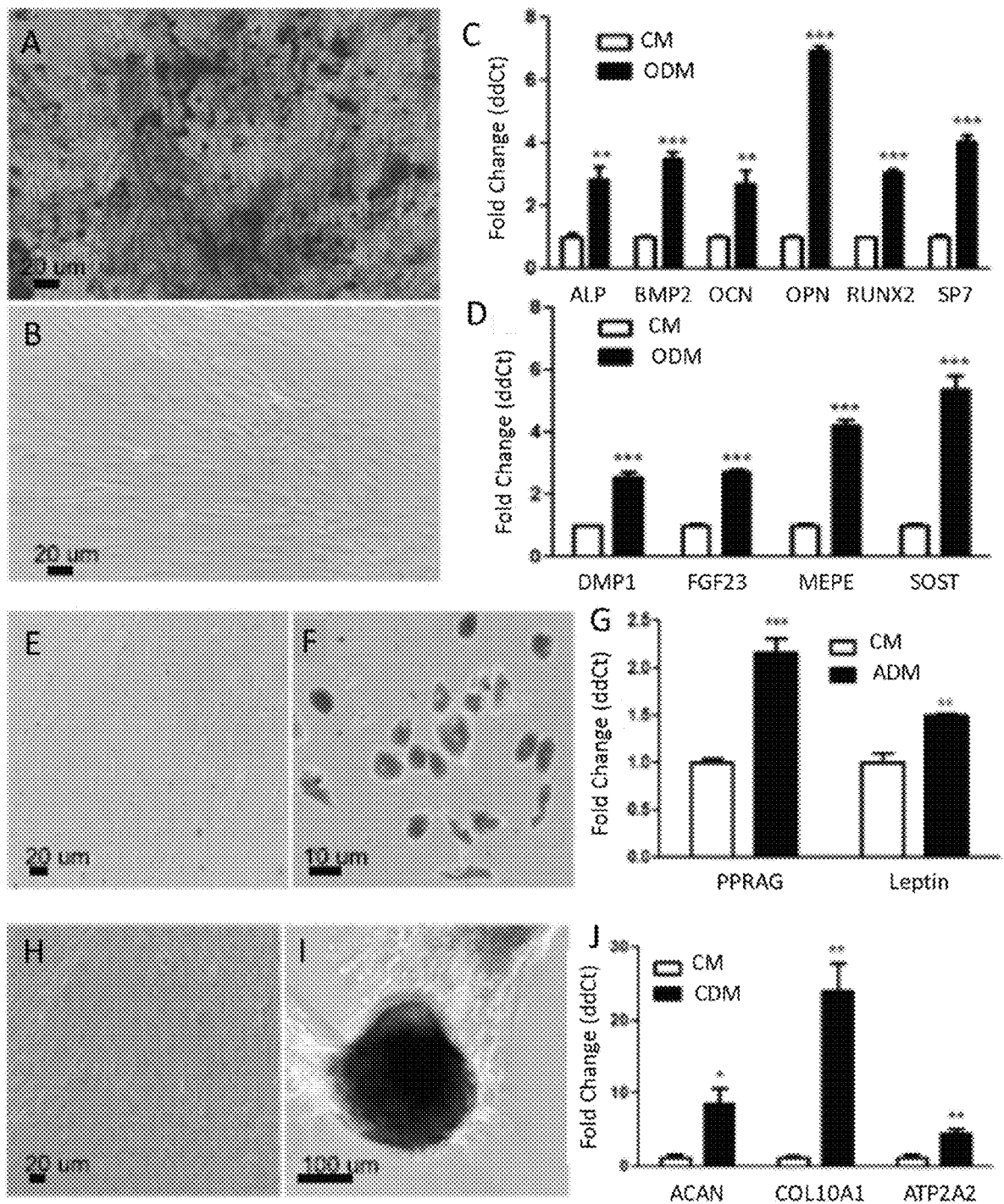
FIG. 4A through FIG. 4J, depicts exemplary experimental results demonstrating osteogenic, chondrogenic, and adipogenic differentiation of T-MPCs.

Undifferentiated MPCs do not secrete calcium deposits, whereas differentiated osteoblasts present massive extracellular calcium deposits both in vivo and in vitro. Therefore, calcium deposits following osteogenic differentiation indicate successful differentiation of MPC into osteoblasts and in vitro bone-formation. To confirm osteogenic differentiation potency of the T-MPCs, cells were grown in osteogenic differentiation medium for 21 days. Following osteogenic induction, the morphology of the MPCs dramatically changed from the fibroblastic phenotype to the expected more flattened type. Differentiated cells are positively stained for Alizarin Red S (FIG. 4a), indicating osteogenic differentiation and extracellular calcium accumulation. Control T-MPCs grown at a similar density for the same time duration in CM were negative (FIG. 4b). Furthermore, RT-qPCR results validate the osteogenic differentiation as a significant upregulation was observed in the osteoblast markers: Alkaline phosphatase (ALP), Bone morphogenetic protein 2 (BMP2), Osteocalcin (OCN), Osteopontin (OPN), Runt-related transcription factor 2 (RUNX2), and Osterix (SP7) (FIG. 4c). Remarkably, following osteogenic differentiation, the results indicate a significant upregulation of osteocyte markers such as Dentin Matrix Protein 1 (DMP1), fibroblast Growth Factor 23 (FGF23), Matrix Extracellular Phospho-glycoprotein (MEPE), and Sclerostin (SOST) (FIG. 4d). The data indicate that T-MPCs can efficiently form early osteoblasts and suggest they progress to form mature osteocytes in culture.

Adipogenesis of T-MPCs

To assess the adipogenesis potential, T-MPCs were grown in adipogenic medium for 21 days. Cells at the same density and for the same culture duration were incubated in CM and used as controls. Major morphological changes were apparent within 5 days of adipogenic differentiation, and typical oil vesicles were observed following 10 days to 2 weeks. Differentiation of T-MPCs into adipocytes was confirmed by Oil Red O staining (FIG. 4e and FIG. 4f), which indicates accumulation of oil droplets consistent with adipocytes. RT-qPCR analyses further validated T-MPC derived adipocytes express increased levels of the adipocyte markers PPRAG and Leptin (FIG. 4g). These results indicate efficient differentiation of T-MPCs into the adipogenic lineage.

Chondrogenic Differentiation of T-MPCs

Next, to confirm differentiation toward cartilage tissue, T-MPCs were grown as attached cell pellets (Yoo et al., (1998) J Bone Joint Surg Am, 80:1745-1757; Johnstone et al., (1998) Exp Cell Res, 238:265-272) in chondrogenic medium for 21 days. T-MPC controls grown in complete medium for the same time were used as controls and showed no staining (FIG. 4h), while TMPC-derived chondrocytes were heavily stained with Alcian blue (FIG. 4i). Total RNA extracted from the differentiated chondrocytes was used to determine the levels of chondrogenic markers. QPCR data validated the differentiation and a significant increase in the chondrogenic markers ACAN, COL10A1 and APT2A2 (FIG. 4j). These data indicate effective differentiation of the T-MPCs into the chondrogenic lineage.

T-MPCS Survive In Vivo but do not Form Teratoma Tumors

Figures 5A, 5B, 5C, 5D, 5E:
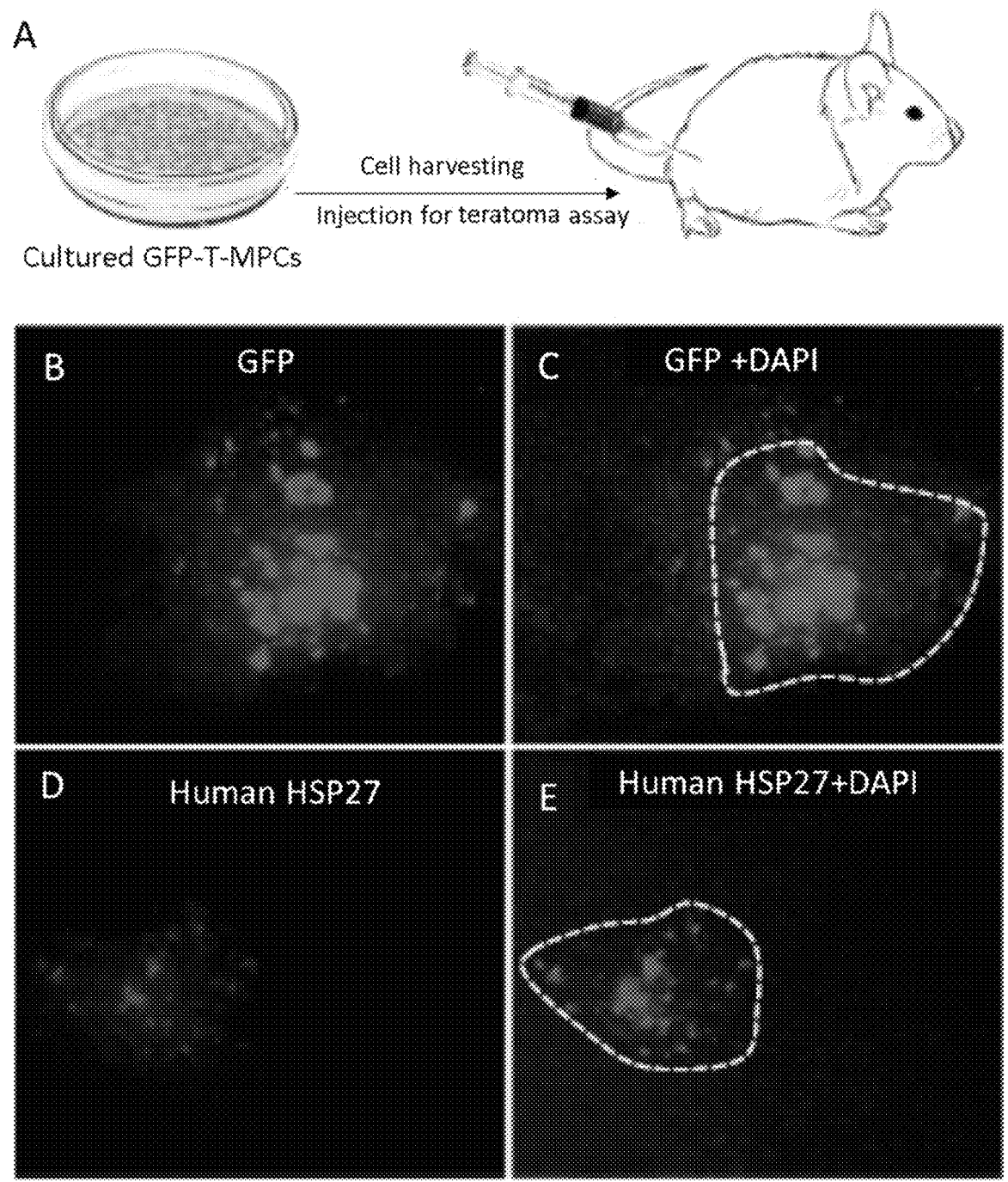
FIG. 5A through FIG. 5E, depicts exemplary experimental results demonstrating that a teratoma assay of engrafted T-MPCs in vivo shows no teratoma in mice.

Unlike pluripotent stem cells, MPCs possess no teratomaforming potential as the cells respond to contact inhibition in vivo and stop dividing upon transplantation. To demonstrate that T-MPCs replicate in vivo, green fluorescent protein (GFP)-positive T-MPCs were generated. The GFP reporter gene allowed tracing of the cells upon the completion of the experiment. Cells were harvested by accutase and resuspended in PBS for injection. A total of ten immunodeficient NOD-SCID gamma mice (8-12 weeks old) were subcutaneously injected with $2 \times 10^6$ T-MPCs per mouse. All mice were monitored for a period of 7 months. Upon termination of the experiment, mice were thoroughly examined and no teratomas were detected in vivo. Cell engraftments in the fat pads were fixed in paraformaldehyde and taken for GFP assessment (FIG. 5a and FIG. 5b) and whole-mount immunofluorescence staining with the human-specific antibody anti-HSP27 (FIG. 5c and FIG. 5d). The results demonstrate that T-MPCs efficiently survived and persisted in the injection site for a prolonged period of time and did not form teratoma tumors.

Previous protocols to generate multipotent progenitor cells (MPCs) from tonsils are limited to discarded tissue following tonsillectomy. Furthermore, the enzymatic digestion by collagenase, accutase or trypsin leads to incomplete tissue dissociation and a low yield (Ryu et al., (2012) Cytotherapy, 14:1193-1202; Janjanin et al., (2008) Arthritis Res Ther 10:R83; Choi et al., (2015) Cell Physiol Biochem, 36:85-99). The experiments presented demonstrate the extraction of MPCs from a small sample of tonsillar tissue (0.88 cc) which can be obtained by a minimally invasive procedure to produce millions of stem cells. Further, T-MPCs can be massively expanded in culture. Extraction of a small sample of less than 1 gram is equivalent to a tonsillar biopsy and will avoid incisions on the body, and minimize risk of infection. Harvesting stem cells from a biopsy sized tissue fragment reduces the need for a major surgical site and the resulting morbidity to the donor. The procedure can be done in the doctor's office in minutes without the need for general anesthetics or hospitalization. It will require a topical and a local anesthetic similar to that of a dental procedure and can be done in a fully awake and healthy donor.

Human MPCs have abilities to modulate the immune response, home to sites of tissue injury, and promote tissue healing and regeneration. Currently, hundreds of clinical trials are in progress exploring applications of stem cells in the treatment of numerous human disease and conditions. However, extensive use of MPCs is limited at present due to the low abundance and viability of the cells during tissue harvesting, and the invasive nature of the current procedures (Francis et al., (2010) Organogenesis, 6:11-4; Zuk et al., (2002) Mol Biol Cell, 13:4279-4295; Jin et al., (2013) Int J Mol Sci, 14:17986-18001, Kim et al., (2015) Differentiation, 90:27-39). Current protocols still rely on tissues discarded during surgical procedures, making mass production and even autologous cells difficult to obtain.

Isolated human tonsil-derived MPCs have been characterized and their robust multipotency has been demonstrated with minimal mechanical and enzymatic insult to the tissue. Further, these cells can be propagated and maintained in xeno-free conditions. Harvest and culture in xeno-free medium will render these cells suitable for cellular therapies and reconstructive procedures in human. Harvesting stem cells from a tonsillar biopsy reduces the need for a major surgical site and is a procedure that can be performed in an outpatient setting, thus having less morbidity compared to bone marrow biopsy or extensive liposuction. Furthermore, it does not rely on discarded tissues from unrelated surgical procedures. Due to the high initial yield, the T-MPCs can be expanded through at least 40 population doublings within approximately 11 weeks. Overall, the studies demonstrate that tonsillar biopsies samples can be used as an excellent, translational source of MPCs for research and clinical applications.

Isolation and culture expansion of adult stem/progenitor cells is a critical step in cell therapy. A large number of stem cells are required for therapeutic uses. Recent studies have shown that MPCs from different anatomical sites differ widely in expression signatures and differentiation potency (Sacchetti et al., (2016) Stem Cell Rep, 6:897-913). Therefore, the tissue source and the derivation process determine the abundance, phenotype, and differentiation potency of MPCs ((Baksh et al., (2007) Stem Cells, 25:1384-92; Heidari et al., (2013) Avicenna J Med Biotechnol, 5:104-117; Heo et al., (2016) Int J Mol Med, 37:115-125; Tan et al., (2012) Tissue Eng Part A, 18:840-851; De Bari et al., (2008) Arthritis Rheum, 58:240-250). This novel procedure achieves a high yield of tonsillar biopsy-derived MPCs with high expansion potential through at least 40 population doublings within a short time. Therefore, these studies indicate that tonsillar biopsies smaller than 1 g of tissue are an excellent, translational source of MPCs for research and clinical applications.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of isolating a tonsillar multipotent progenitor cell (T-MPC) from a tonsillar tissue comprising the steps of:
   a) contacting a tonsillar tissue with a digestion solution comprising a combination of Collagenase I, Collagenase II, thermolysin, and a deoxyribonuclease, wherein the tonsillar tissue is obtained from a tonsil biopsy sample, wherein the tonsillar tissue sample is less than 2.0 cubic centimeters; and
   b) separating the T-MPCs,
wherein the yield of T-MPCs is at least $2 \times 10^8$ cells per gram of tissue.

2. The method of claim 1, wherein the method of separating the T-MPCs comprises the steps of centrifuging the cells and selecting cells having the lowest density.

3. The method of claim 1, wherein the method of separating comprises fluorescence-activated cell sorting.

4. The method of claim 3, wherein the sorted cells express at least one marker selected from the group consisting of CD44, CD90, CD73, CD105, TRA-1-80, and TRA- 1-60.

5. The method of claim 1, wherein the isolated T-MPCs are at least 80% pure, at least 85% pure, at least 90% pure, at least 95% pure, at least 97% pure, at least 98% pure, at least 99% pure, at least 99.5% pure, or at least 99.9% pure T-MPCs.

6. The method of claim 1, wherein the tonsillar tissue sample is 1.0 cubic centimeters or less.

* * * * *

```
                              SEQUENCE LISTING

<160> NUMBER OF SEQ ID NOS: 30

<210> SEQ ID NO 1
<211> LENGTH: 22
<212> TYPE: DNA
<213> ORGANISM: Artificial Sequence
<220> FEATURE:
<223> OTHER INFORMATION: BMP2 Forward Primer

<400> SEQUENCE: 1
ccctacatgc tagacctgta tc                                                22

<210> SEQ ID NO 2
<211> LENGTH: 22
<212> TYPE: DNA
<213> ORGANISM: Artificial Sequence
<220> FEATURE:
<223> OTHER INFORMATION: BMP2 Reverse Primer

<400> SEQUENCE: 2
gttgttttcc cactcgtttc tg                                                22

<210> SEQ ID NO 3
<211> LENGTH: 22
<212> TYPE: DNA
<213> ORGANISM: Artificial Sequence
<220> FEATURE:
<223> OTHER INFORMATION: OPN Forward Primer

<400> SEQUENCE: 3
ccttccaagt aagtccaacg aa                                                22

<210> SEQ ID NO 4
<211> LENGTH: 22
<212> TYPE: DNA
<213> ORGANISM: Artificial Sequence
<220> FEATURE:
<223> OTHER INFORMATION: OPN Reverse Primer

<400> SEQUENCE: 4
gacaactgga gtgaaaactt cg                                                22

<210> SEQ ID NO 5
<211> LENGTH: 21
<212> TYPE: DNA
<213> ORGANISM: Artificial Sequence
<220> FEATURE:
<223> OTHER INFORMATION: OCN Forward Primer

<400> SEQUENCE: 5
atgagagccc tcacactcct c                                                 21

<210> SEQ ID NO 6
<211> LENGTH: 21
<212> TYPE: DNA
<213> ORGANISM: Artificial Sequence
<220> FEATURE:
<223> OTHER INFORMATION: OCN Reverse Primer

<400> SEQUENCE: 6
gccgtagaag cgccgatagg c                                                 21
```

<210> SEQ ID NO 7
<211> LENGTH: 24
<212> TYPE: DNA
<213> ORGANISM: Artificial Sequence
<220> FEATURE:
<223> OTHER INFORMATION: ALP Forward Primer

<400> SEQUENCE: 7
tggagcttca gaagctcaac acca                                              24

<210> SEQ ID NO 8
<211> LENGTH: 24
<212> TYPE: DNA
<213> ORGANISM: Artificial Sequence
<220> FEATURE:
<223> OTHER INFORMATION: ALP Reverse Primer

<400> SEQUENCE: 8
atctcgttgt ctgagtacca gtcc                                              24

<210> SEQ ID NO 9
<211> LENGTH: 20
<212> TYPE: DNA
<213> ORGANISM: Artificial Sequence
<220> FEATURE:
<223> OTHER INFORMATION: RUNX2 Forward Primer

<400> SEQUENCE: 9
tttagggcgc attcctcatc                                                   20

<210> SEQ ID NO 10
<211> LENGTH: 17
<212> TYPE: DNA
<213> ORGANISM: Artificial Sequence
<220> FEATURE:
<223> OTHER INFORMATION: RUNX2 Reverse Primer

<400> SEQUENCE: 10
ggagggccgt gggttct                                                      17

<210> SEQ ID NO 11
<211> LENGTH: 22
<212> TYPE: DNA
<213> ORGANISM: Artificial Sequence
<220> FEATURE:
<223> OTHER INFORMATION: FGF23 Forward Primer

<400> SEQUENCE: 11
ttggatcaca ctatttcgac cc                                                22

<210> SEQ ID NO 12
<211> LENGTH: 22
<212> TYPE: DNA
<213> ORGANISM: Artificial Sequence
<220> FEATURE:
<223> OTHER INFORMATION: FGF23 Reverse Primer

<400> SEQUENCE: 12
gaagtgaatt aggggatct cg                                                 22

<210> SEQ ID NO 13
<211> LENGTH: 22
<212> TYPE: DNA
<213> ORGANISM: Artificial Sequence
<220> FEATURE:
<223> OTHER INFORMATION: DMP1 Forward Primer

```
<400> SEQUENCE: 13
tctttgtgaa ctacggaggg ta                                              22

<210> SEQ ID NO 14
<211> LENGTH: 20
<212> TYPE: DNA
<213> ORGANISM: Artificial Sequence
<220> FEATURE:
<223> OTHER INFORMATION: DMP1 Reverse Primer

<400> SEQUENCE: 14
tgagccaaat gacccttcca                                                 20

<210> SEQ ID NO 15
<211> LENGTH: 24
<212> TYPE: DNA
<213> ORGANISM: Artificial Sequence
<220> FEATURE:
<223> OTHER INFORMATION: MEPE Forward Primer

<400> SEQUENCE: 15
gaggaaaagg tagactgaga ttct                                            24

<210> SEQ ID NO 16
<211> LENGTH: 24
<212> TYPE: DNA
<213> ORGANISM: Artificial Sequence
<220> FEATURE:
<223> OTHER INFORMATION: MEPE Reverse Primer

<400> SEQUENCE: 16
gggacaaatc tttctttctt tcct                                            24

<210> SEQ ID NO 17
<211> LENGTH: 22
<212> TYPE: DNA
<213> ORGANISM: Artificial Sequence
<220> FEATURE:
<223> OTHER INFORMATION: SOST Forward Primer

<400> SEQUENCE: 17
caagaatgat gccacggaaa tc                                              22

<210> SEQ ID NO 18
<211> LENGTH: 20
<212> TYPE: DNA
<213> ORGANISM: Artificial Sequence
<220> FEATURE:
<223> OTHER INFORMATION: SOST Reverse Primer

<400> SEQUENCE: 18
ggacacgtct ttggtctcaa                                                 20

<210> SEQ ID NO 19
<211> LENGTH: 23
<212> TYPE: DNA
<213> ORGANISM: Artificial Sequence
<220> FEATURE:
<223> OTHER INFORMATION: RPLP0 Forward Primer

<400> SEQUENCE: 19
cagcaagtgg gaaggtgtaa tcc                                             23

<210> SEQ ID NO 20
```

```
<211> LENGTH: 25
<212> TYPE: DNA
<213> ORGANISM: Artificial Sequence
<220> FEATURE:
<223> OTHER INFORMATION: RPLP0 Reverse Primer

<400> SEQUENCE: 20
cccattctat catcaacggg tacaa                                         25

<210> SEQ ID NO 21
<211> LENGTH: 22
<212> TYPE: DNA
<213> ORGANISM: Artificial Sequence
<220> FEATURE:
<223> OTHER INFORMATION: ACAN Forward Primer

<400> SEQUENCE: 21
tgatgttccc tgcaattacc ac                                            22

<210> SEQ ID NO 22
<211> LENGTH: 22
<212> TYPE: DNA
<213> ORGANISM: Artificial Sequence
<220> FEATURE:
<223> OTHER INFORMATION: ACAN Reverse Primer

<400> SEQUENCE: 22
caaaaagcga caagaagagg ac                                            22

<210> SEQ ID NO 23
<211> LENGTH: 24
<212> TYPE: DNA
<213> ORGANISM: Artificial Sequence
<220> FEATURE:
<223> OTHER INFORMATION: Leptin Forward Primer

<400> SEQUENCE: 23
attttcagaa gagaacggac attc                                          24

<210> SEQ ID NO 24
<211> LENGTH: 22
<212> TYPE: DNA
<213> ORGANISM: Artificial Sequence
<220> FEATURE:
<223> OTHER INFORMATION: Leptin Reverse Primer

<400> SEQUENCE: 24
tgctcccctt cttcaaaatg ta                                            22

<210> SEQ ID NO 25
<211> LENGTH: 22
<212> TYPE: DNA
<213> ORGANISM: Artificial Sequence
<220> FEATURE:
<223> OTHER INFORMATION: ATP2A2 Forward Primer

<400> SEQUENCE: 25
aactacctgg aacctgcaat ac                                            22

<210> SEQ ID NO 26
<211> LENGTH: 22
<212> TYPE: DNA
<213> ORGANISM: Artificial Sequence
<220> FEATURE:
<223> OTHER INFORMATION: ATP2A2 Reverse Primer

<400> SEQUENCE: 26
```

```
gggttggtag atgtgttgct aa                                              22

<210> SEQ ID NO 27
<211> LENGTH: 25
<212> TYPE: DNA
<213> ORGANISM: Artificial Sequence
<220> FEATURE:
<223> OTHER INFORMATION: COL10A1 Forward Primer

<400> SEQUENCE: 27
gagtaaaggt atagcagtaa gagga                                           25

<210> SEQ ID NO 28
<211> LENGTH: 22
<212> TYPE: DNA
<213> ORGANISM: Artificial Sequence
<220> FEATURE:
<223> OTHER INFORMATION: COL10A1 Reverse Primer

<400> SEQUENCE: 28
catatggtcc tctctctcct gg                                              22

<210> SEQ ID NO 29
<211> LENGTH: 22
<212> TYPE: DNA
<213> ORGANISM: Artificial Sequence
<220> FEATURE:
<223> OTHER INFORMATION: PPRAG Forward Primer

<400> SEQUENCE: 29
aagacaacag acaaatcaac cg                                              22

<210> SEQ ID NO 30
<211> LENGTH: 22
<212> TYPE: DNA
<213> ORGANISM: Artificial Sequence
<220> FEATURE:
<223> OTHER INFORMATION: PPRAG Reverse Primer

<400> SEQUENCE: 30
gtcttcttga tcacctgcag ta                                              22
```